US007196385B2

(12) United States Patent
Bureau et al.

(10) Patent No.: US 7,196,385 B2
(45) Date of Patent: Mar. 27, 2007

(54) MICROSTRUCTURE COMPRISING A SURFACE WHICH IS FUNCTIONALIZED THROUGH THE LOCALIZED DEPOSIT OF A THIN LAYER AND PRODUCTION METHOD THEREOF

(75) Inventors: Christophe Bureau, Suresnes (FR); Christophe Kergueris, Paris (FR); Francois Perruchot, Issy les Moulineaux (FR)

(73) Assignees: Alchimer S.A., Massy (FR); Tronic's Microsystems, Grenoble (FR)

( * ) Notice: Subject to any disclaimer, the term of this patent is extended or adjusted under 35 U.S.C. 154(b) by 0 days.

(21) Appl. No.: 10/524,560

(22) PCT Filed: Aug. 25, 2003

(86) PCT No.: PCT/FR03/50036

§ 371 (c)(1),
(2), (4) Date: Feb. 14, 2005

(87) PCT Pub. No.: WO2004/018349

PCT Pub. Date: Mar. 4, 2004

(65) Prior Publication Data

US 2005/0253206 A1    Nov. 17, 2005

(30) Foreign Application Priority Data

Aug. 26, 2002  (FR) ................................. 02 10571

(51) Int. Cl.
*H01L 29/84* (2006.01)
*H01L 21/00* (2006.01)
(52) U.S. Cl. .................... 257/419; 977/733; 438/53
(58) Field of Classification Search .............. 257/419; 438/53; 977/733
See application file for complete search history.

(56) References Cited

U.S. PATENT DOCUMENTS

| 4,722,348 A | 2/1988 | Ligtenberg et al. |
| 5,067,491 A | 11/1991 | Taylor, II et al. |
| 5,512,374 A | 4/1996 | Wallace et al. |

(Continued)

FOREIGN PATENT DOCUMENTS

| EP | 0 241 294 | 10/1987 |
| FR | 2 771 551 | 5/1999 |
| WO | 00/57467 | 9/2000 |

OTHER PUBLICATIONS

U.S. Appl. No. 10/544,651, filed Aug. 5, 2005, Bureau et al.
U.S. Appl. No. 10/524,560, filed Feb. 14, 2005, Bureau et al.
Cui, Xinyan et al. "Electrochemical deposition and characterization of conducting polymer polypyrrole/PSS on multichannel neural probes", Sensors and Actuators A, vol. 93, No. 1, pp. 8-18.

(Continued)

*Primary Examiner*—Andy Huynh
*Assistant Examiner*—Earl Taylor
(74) *Attorney, Agent, or Firm*—Oblon, Spivak, McClelland, Maier & Neustadt, P.C.

(57) ABSTRACT

An electromechanical microstructure including a first mechanical part formed in a first electrically conductive material, and which includes a zone deformable in an elastic manner having a thickness value and an exposed surface, and a first organic film having a thickness, present on all of the exposed surface of the deformable zone. The thickness of the first film is such that the elastic response of the deformable zone equipped with the first film does not change by more than 5% compared to the response of the bare deformable zone, or the thickness of the first film is less than ten times the thickness of the deformable zone.

44 Claims, 9 Drawing Sheets

U.S. PATENT DOCUMENTS 5,567,297 A    10/1996    Mertens et al.
6,137,183 A    10/2000    Sako
6,331,163 B1    12/2001    Kaplan

OTHER PUBLICATIONS

Walter, Peter et al. "Development of a Completely Encapsulated Intraocular Pressure Sensor", Ophthalmic Res., vol. 32, pp. 278-284, 2000.

Man, P.F. et al. "Microfluidic Plastic Capillaries on Silicon Substrates: A New Inexpensive Technology for Bioanalysis Chips", MEMS Conference, pp. 311-316, 1997.

Delamarche, E. et al. "Real-Space Observation of Nanoscale Molecular Domains in Self-Assembled Monolayers", Langmuir, vol. 10, pp. 2869-2871, 1994.

Kumar, Amit et al. "Features of gold having micrometer to centimeter dimensions can be formed through a combination of stamping with an elastomeric stamp and an alkanethiol "ink" followed by chemical etching", Appl. Phys. Lett., vol. 63, No. 14, pp. 2002-2004, 1993.

Renard, S. et al. "Miniature Pressure Acquisition Microsystem for Wireless *In Vivo Measurements*", 1st Annual International IEEE-EMBS Special Topic Conference on Microtechnologies in Medicine & Biology, pp. 175-179, 2000.

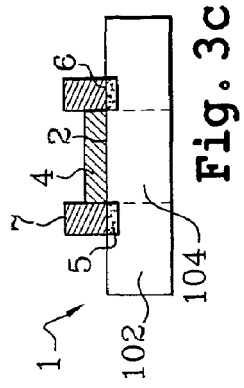 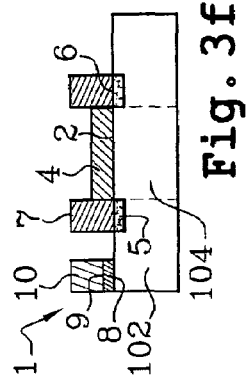 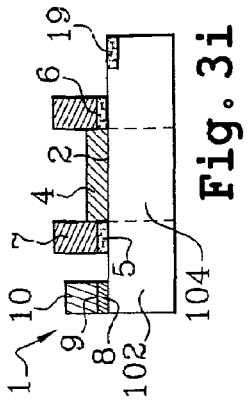
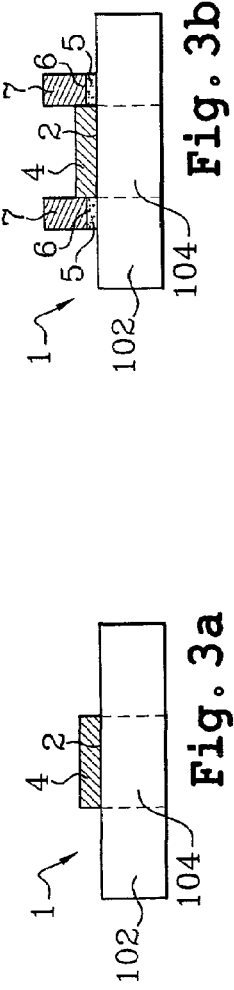
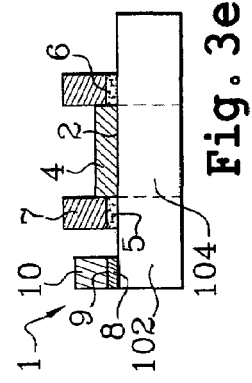 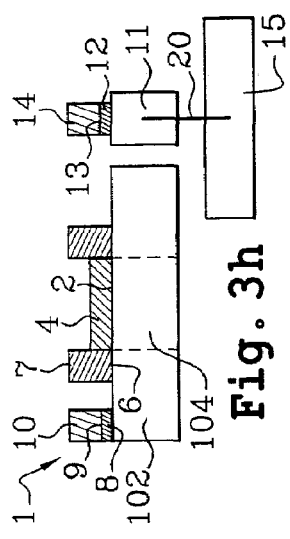
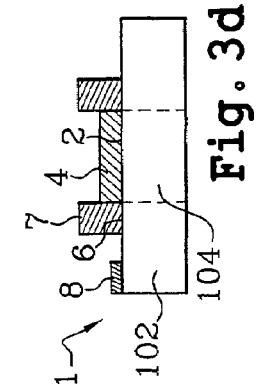 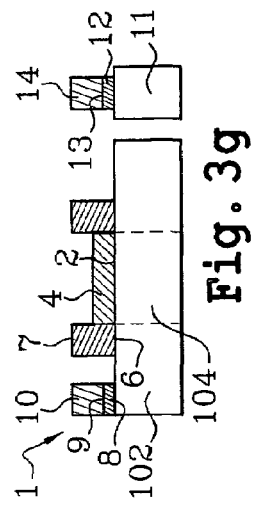

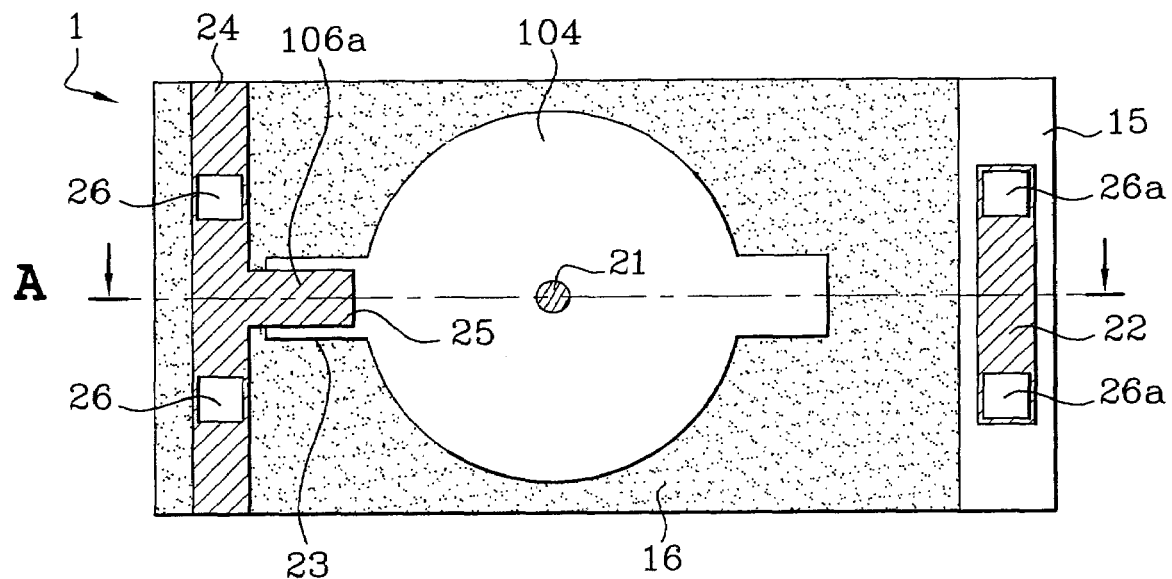
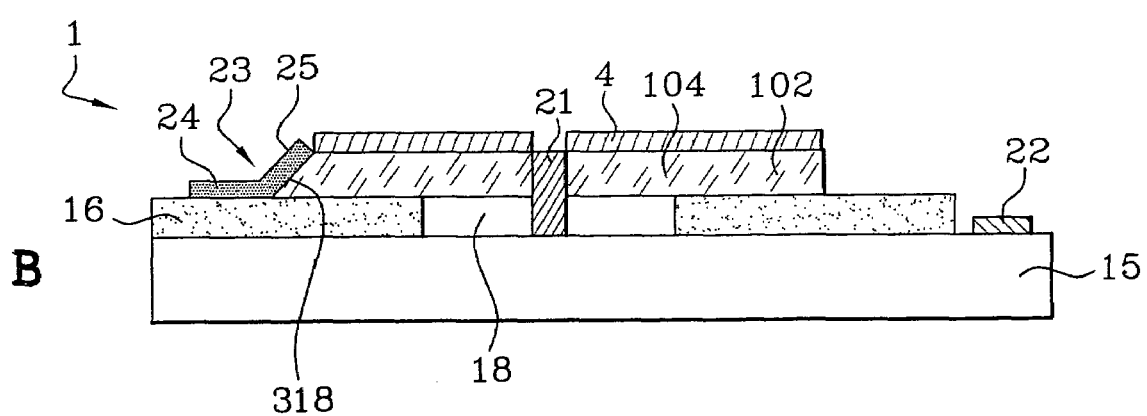
Fig. 5

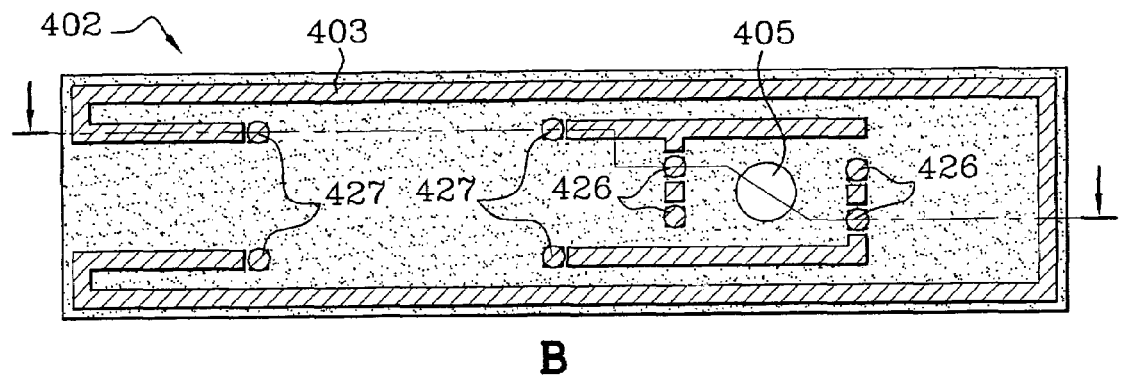
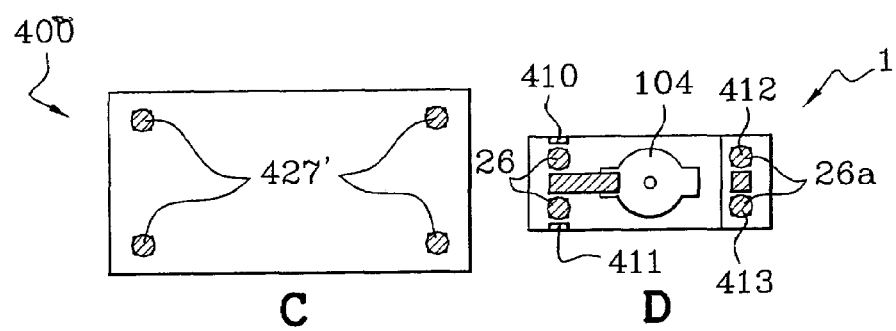
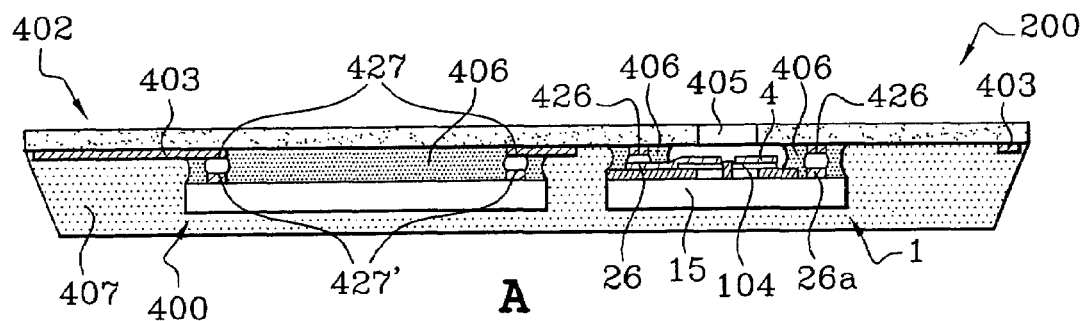
Fig. 6

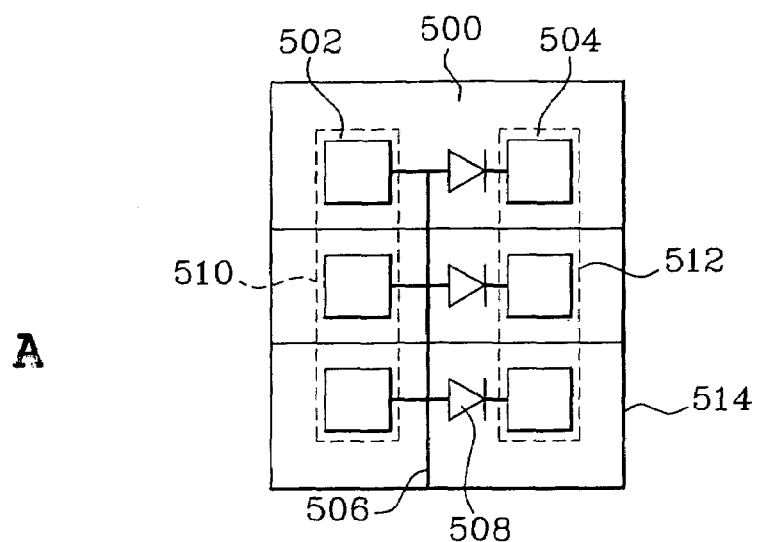
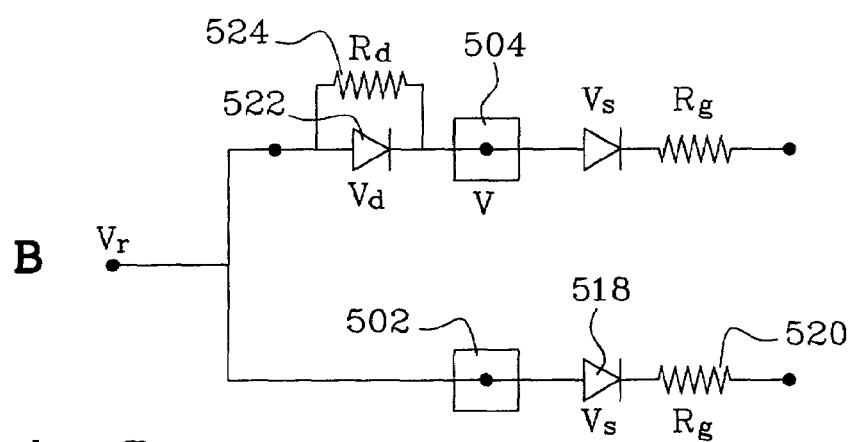
Fig. 7
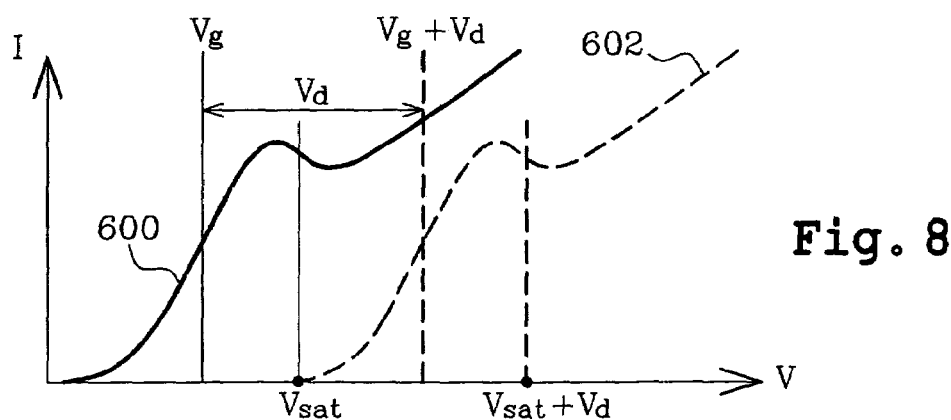
Fig. 8

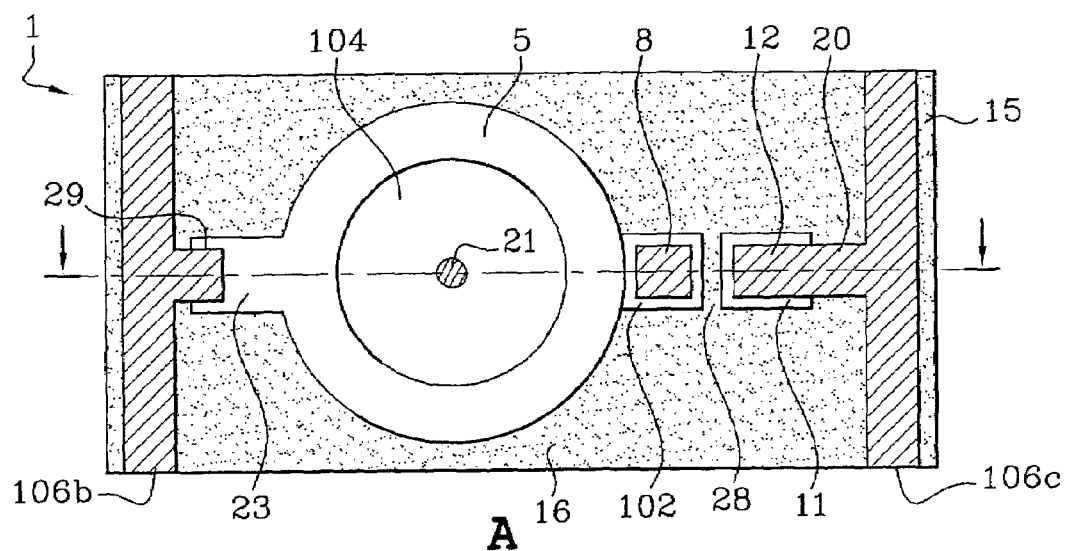
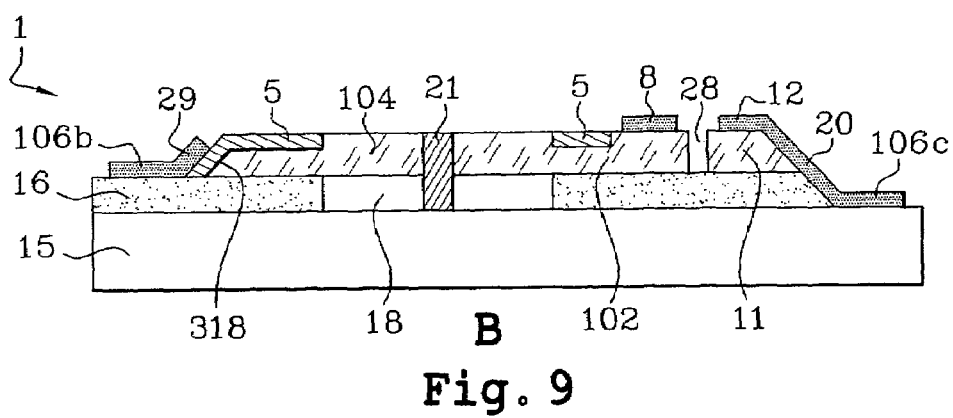
Fig. 9
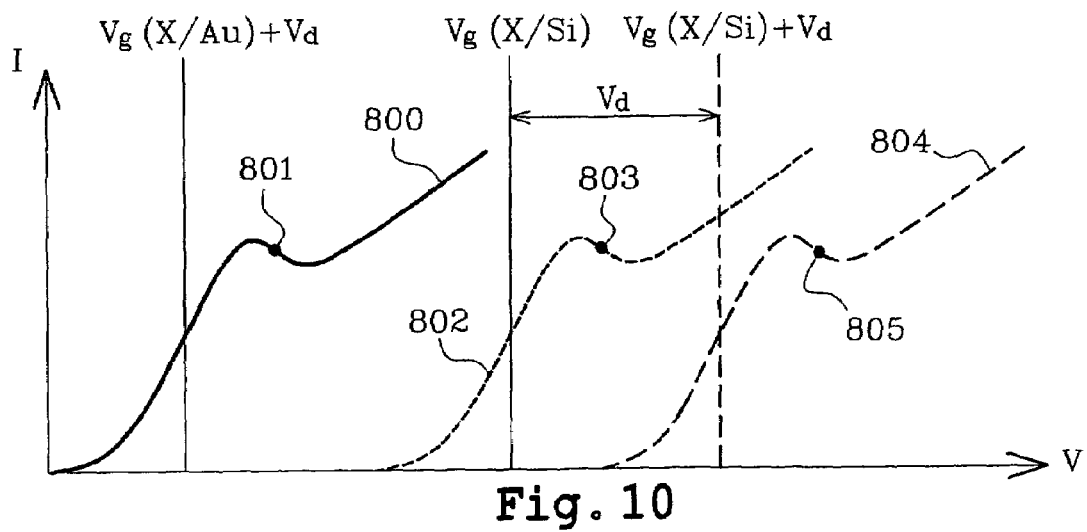
Fig. 10

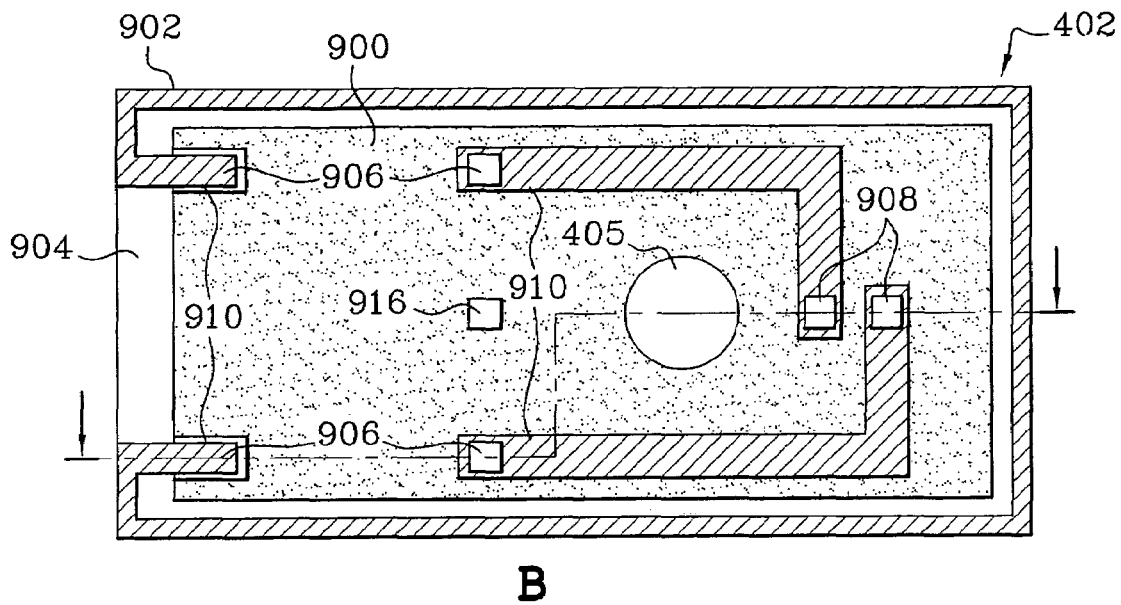
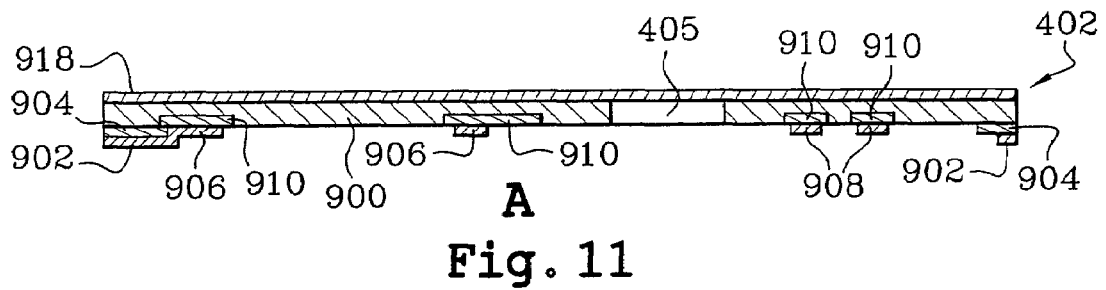
Fig. 11
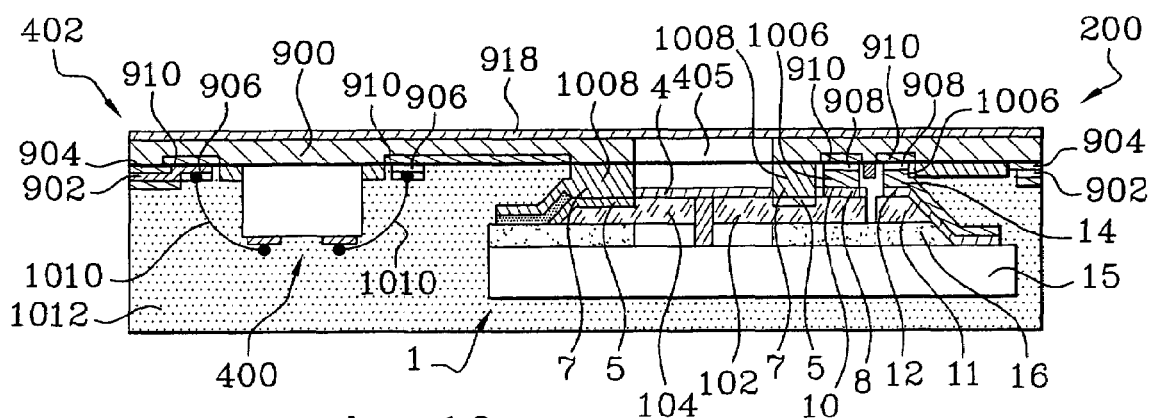
Fig. 12

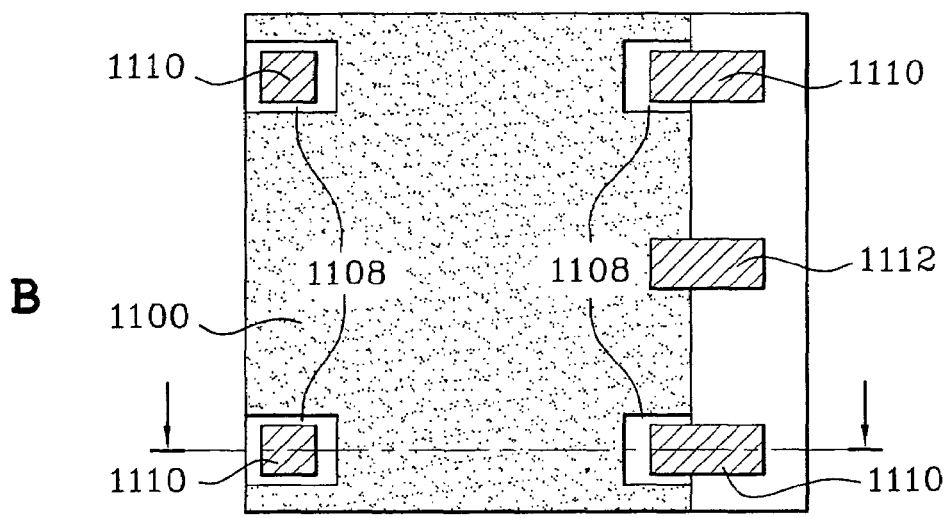
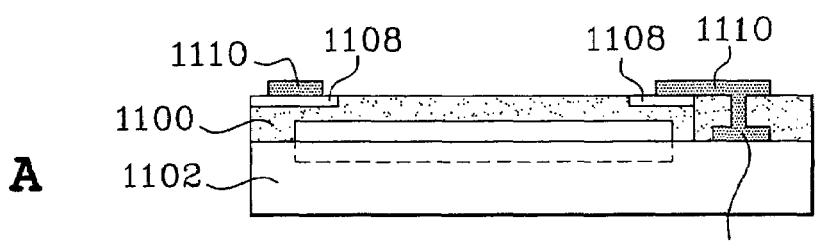
Fig. 13
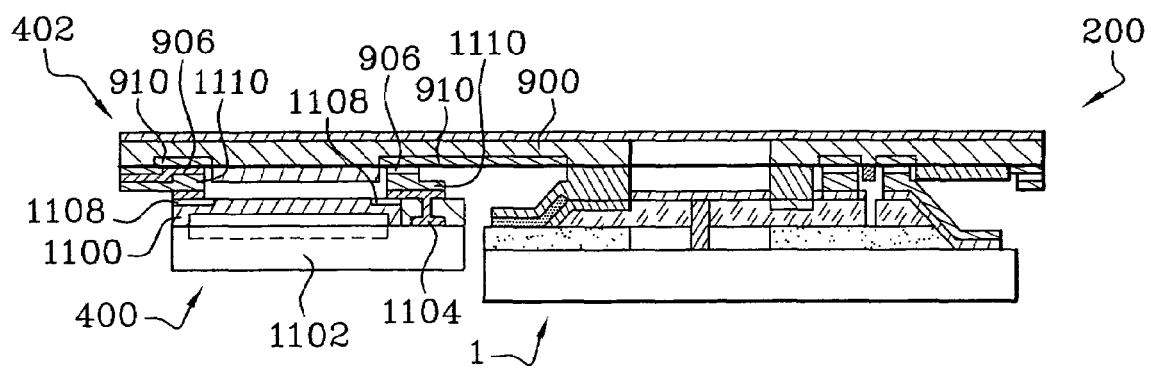
Fig. 14

MICROSTRUCTURE COMPRISING A SURFACE WHICH IS FUNCTIONALIZED THROUGH THE LOCALIZED DEPOSIT OF A THIN LAYER AND PRODUCTION METHOD THEREOF

TECHNICAL FIELD

The invention relates to the field of microcomponents comprising an electromechanical microstructure produced by micromachining and a functionalisation provided by an organic layer formed on the surface. In particular, the invention concerns the field of sensors.

STATE OF THE PRIOR ART

The present invention applies to electromechanical microstructures, produced by micromachining using known MEM techniques (MicroElectroMechanical Systems) based on the use of successive masks to carry out localised operations of chemical or mechanical micromachining. These microstructures, when they comprise a mechanical element that deforms in an elastic manner under the effect of a force, associated with means for measuring the displacement, may for example be used as force sensors, pressure sensors, acceleration sensors, contact sensors, stress gauges, etc.

The use in particular of structures micromachined on monocrystalline silicon makes it possible to obtain elements having very high mechanical performance (absence of hysteresis, purely elastic response without plastic deformation) with very small sizes (around one millimeter).

It is often necessary to provide additional functions to these structures from thin films deposited in a local manner on the surface.

By way of illustration, the electromechanical microstructures manufactured by micromachining of silicon are used for miniature pressure sensors that could be used in vivo in the medical field, in particular when they are integrated within microsystems (component integration, measurement, signal processing and communication functions). Traditional techniques for encapsulating pressure sensors, such as for example encapsulation within a deformable impervious cell filled with an oil bath, are not suitable for these microstructures when the final size of the component is a critical parameter. Pressure sensors may be used, like chemical sensors, with the sensitive part of the sensor—a membrane—in direct contact with the medium to be characterised.

Therefore, it may be necessary to functionalise this part of the sensor to confer it with specific properties vis-à-vis its environment.

This is an example of a specific function that may be added to an electromechanical microstructure by providing it with localised thin film deposits. In a more general but non-exhaustive manner, the following functionalisations may be introduced to this type of component. One may cite:
  the protection of a zone in contact with the exterior vis-à-vis its environment,
  the modification of the chemical properties of a zone in contact with the exterior to make it compatible with its environment (biocompatibility, lubrication to facilitate the installation, absence of degradation, etc.),
  the preparation of the mechanical assembly of the component (assembly of chips between each other, assembly of chips on substrates),
  the preparation of the electrical interconnection with another component (electrical contact between chips, electrical contact between chips and substrates).

General Problem of Preconditioning

The objective of the preconditioning step is, in a general manner, to obtain a functionalisation of the surface of the microstructures thus making it possible to facilitate the subsequent conditioning steps. When this step is collective, it enables the final cost of the component to be reduced. The virtue of a preconditioning method is judged, apart from its cost, by the simplification that it allows to the subsequent conditioning steps.

Different known preconditioning methods exist today that make it possible to introduce different functions to these types of microstructures or components, in particular when they are intended to be assembled in a compact manner within a microsystem.

Functionalisation of the Membrane

To introduce specific properties to the sensitive element of an electromechanical microstructure from the deposition of a thin film, a known method is the functionalisation of the membrane of a sensor from a thin film formed in liquid phase by dipping or by centrifugation. These techniques may for example be used for depositing silicones (PDMS type, for example) for pressure sensors used in vivo for medical applications [Development of a completely encapsulated intraocular pressure sensor, Walter P. et al, Ophthalmic Research (2000), 32, p 278–284].

Another known method is the chemical vapour deposition (CVD) of a layer of polymer. One knows for example depositing by this technique a specific polymer, parylene, known for its biocompatibility properties [Microfluidic plastic capillaries on silicon substrates: a new inexpensive technology for bioanalysis chips, P. F. Man et al, presented at the MEMS Conference 1997, Jan. 26–30 1997, Nagoya, Japan].

These techniques are difficult to tally with a specification imposed on the microstructure, in particular when it is used to form a high precision sensor that has to be used for long periods without calibration.

These techniques make difficult the precise control of the thickness formed and the homogeneity of the deposit for low thicknesses. Moreover, since the bond between the layer and the surface to be functionalised is not a covalent bond, the functional qualities of the layer are only assured for significant thicknesses. Consequently, it is difficult to assure, from these known techniques, a functional layer that does not change the mechanical performance of the microstructure, in particular if the mechanical element is formed in monocrystalline silicon with thicknesses less than ten or so microns.

For example, the films formed by plasma deposition of a parylene film are recognised as uniform, without perforations, with a low permeability to mould and good dielectric properties for thicknesses greater than 10 microns and it is difficult to control a thickness to better than several microns. For structures in which the membrane is of a typical thickness of several microns, a film of thickness greater than 5 µm reduces the sensitivity of the sensor by a factor of more than 2. Moreover, it is recognised that the adhesion of the parylene films is of mediocre quality.

The layers formed by deposition of silicones are excellent for a short term protection but rapidly degrade over time. The problem of air bubbles that are trapped in the layer is at the origin of adhesion defects that extend over time.

It should be pointed out that it is also difficult to use these techniques to form selective deposits in a collective manner without resorting to the implementation of complex and costly mechanical masks.

Laboratory techniques based on the functionalisation of a surface from covalent bonds are known to answer the problems of adhesion of the layers and efficiency at low thickness: single layers self-assembled by dipping or by microcontact printing [Delamarche E., Michel B., Gerber Ch., Langmuir (1994), 10, p 2869 and Kumar A., Whitesides G. M., Applied Physics Letters (2002), 63, p 1993]. These techniques are restricted to several film material—surface material pairs (even if they can sometimes act as a primer for the anchoring of other molecular materials) such as for example thiols on gold, silanes on silica or more generally oxide layers. Although known, the problems linked to their use means that they are not often used industrially.

In a general manner, the existing techniques restrict the choice of properties of materials that could be used and make the selective deposition and the control of the thickness difficult.

Preparation of the Electrical Interconnection

To form the electrical interconnection between the microstructure and a substrate or another component, the "flip-chip" technique is known. The electrical and mechanical interconnection is achieved by means of bosses of fusible conductive material formed on the bond pads of the microstructure and welded by a thermal treatment of the bond pads of the transfer substrate arranged opposite.

The known preconditioning associated with this micropackaging method comprises the preparation of bosses by different methods: collective methods by electrodeposition, evaporation, screen printing, methods . . . or individual methods by stamping, dispensing, etc., from different materials (fusible material with or without lead, fusible polymer, etc.).

The known techniques are satisfactory with regard to the aspect of thickness of the layer, which is not critical for this functionalisaton, but the mechanical bond assured by the boss must be made reliable during the conditioning in most applications since the different deposition methods used do not assure a good mechanical bond between the substrate and the boss. Moreover, these techniques, developed for electronic components, are less well suited to the microstructures when their contact pad is of a size less than one hundred or so microns.

The reliability of the mechanical interconnections may be improved by application of a dielectric filling material, or "underfill", between the chip and the substrate, which makes it possible to absorb the difference in the thermal dilation coefficients of the chip and of the substrate.

This method uses an additional step after the preconditioning taking place after the transfer and is therefore non collective and difficult to implement for microstructures of small dimensions and having on the same face bond pads and a sensitive surface (sensor).

To resolve this problem there exists, for example (WO 0057467), solutions that make it possible to apply, during the preconditioning, the filling material on all of the surface of a wafer of chips before its dissociation by carrying out a selective coating of an adhesive material excluding the contact point zones of each chip. The selective coating may be carried out, before or after formation of bosses on the contact points, by screen printing or by jet of material. The delicate step of filling by capillarity the interstice located between the chip and the substrate in an individual manner after the transfer of the chip is thus avoided.

Preconditioning solutions also exist (U.S. Pat. No. 6,137,183), consisting in applying on all of the surface of a wafer of chips before their dissociation an anisotropic conductive adhesive, as a film or a paste. In this way, the electrical and mechanical interconnections are formed in a single step.

The methods described above only make it possible to prepare the components for the mechanical and electrical assembly steps. Consequently, they must be associated with a different method to carry out the operations of protection or functionalisation of the mechanical parts.

DESCRIPTION OF THE INVENTION

There is therefore a need for microstructures comprising on the surface functionalisations formed from a local thin film deposition of material. Since these microstructures are formed in a collective manner on a wafer, there exists a need for wafers adapted to the collective treatment of these components.

The present invention concerns an electromechanical microstructure formed in general in a collective manner by micromachining on which are added one or several functions introduced by the localised deposition of a thin film. The thin film deposited has good adhesion properties at the surface of the deposit, the bond being a covalent bond. The thicknesses of the materials introduced and their homogeneity are well controlled. It thus becomes possible to guarantee a good reproducibility and stable performance over time. Contrary to the prior art, all of the advantages introduced are introduced simultaneously, without one being obtained to the detriment of the other.

The present invention also concerns a wafer allowing the collective functionalisation of microstructures or electromechanical chips or electronic chips and substrates before the micropackaging, packaging or assembly steps carried out during the conditioning. A "chip" is taken to mean a miniaturised element manufactured in a collective manner (by batch) for example with known electronic and/or microelectronic technologies.

The wafer allows in a more general manner the collective functionalisation of electronic or electromechanical components from a technique of localised deposition of a thin film. The wafers according to the invention are particularly suited to the collective preconditioning of components before their assembly within microsystems.

The wafer described here enables a chip to be preconditioned in a collective manner (therefore at low unit cost), in an extremely small size (substantially of the size of the pattern of the chip). It enables multiple functionalities to be introduced to the chip by the use of a generic technique enabling the problems of encapsulation and interconnection to be facilitated in an overall manner. It imposes no restriction on the size of the components and the surfaces to be treated. The preconditioning of the chips or microstructures of the wafer degrades in a negligible manner the performance of each chip or microstructure compared to their performance before preconditioning.

The aim of the invention is to propose a high precision electromechanical microstructure with elastic deformation comprising functions provided by localised electrochemical deposition of a thin organic film on the surface of the elastic part. The use of organic layers can potentially provide a considerable choice of functions stemming from organic chemistry.

A further aim of the invention is to propose such a microstructure that may comprise different functions provided by organic films, including outside of the elastic part without substantial degradation of the intrinsic characteristics of the component.

A final aim of the invention is to propose a microcomponent formed from a microstructure assembled on a support.

In order to attain these aims, the subject of the invention is, more precisely, an electromechanical microstructure comprising a first part known as the mechanical part formed in a first electrically conductive material, and which further comprises a zone deformable in an elastic manner having a thickness value and an exposed surface, and on the other hand a first organic film having a thickness, present on all of the exposed surface of said deformable zone, characterised in that the thickness of the first film is such that the elastic response of the deformable zone equipped with the first film does not change by more than 5% compared to the response of the bare deformable zone or in that the thickness of the first film is less than ten times the thickness of the deformable zone.

A thickness of the first film may be chosen so as not to modify the elastic response of the deformable zone equipped with the first film or so as not to modify the stability over time of the elastic response of the deformable zone equipped with the first film. This choice must take account of the quality desired for the deformable zone equipped with the first film, the mechanical effect of the film and the fluctuations over time associated with it. This leads to limiting the modification arising from the film at values respectively less than 1% or 5%.

These conditions may also be reflected in terms of thickness of film, which must not exceed ten times the thickness of the deformable elastic zone in first material for the most flexible films to two times for films of intermediate elasticity.

The organic film is bonded in a covalent manner to the surface of the deformable zone in order to obtain a high adhesion and guarantee its functionality from low thicknesses.

The organic film is preferentially formed from an electro-initiated chemical reaction enabling the electrografting of monomers on the conductive surface, initiating the anchoring or the growth of an insulating organic molecule of given length. This technique makes it possible to ensure both the spatial localisation of the film and to control its thickness. The films are preferentially formed with a high coverage rate, making the layers homogenous and dense.

This first film may provide simultaneously different types of functions at the surface of the deformable zone, such as a chemical protection of the surface or a functionalisation ensuring different chemical properties.

In a specific embodiment, the microstructure comprises different organic films on different parts, including on non-elastic parts. These organic films may combine different properties, such as conductor or insulator, lubricant, adhesive—making it possible to facilitate the conditioning of the microstructure.

The invention may be applied to the realisation of a sensor comprising an electromechanical microstructure micromachined on a semi-conductor. This sensor may for example be a pressure sensor, a tactile sensor or a strain gauge.

The introduction of non-cyctotoxicity and cellular anti-adhesion functions at the surface of the deformable zone of the sensor enable for example its use in the biomedical field.

The functionalisation of the surface of the electrical contacts with an adhesive or thermofusible coating enables an electrical or mechanical assembly of the electromechanical microstructure on a support. The formation of a sealing joint with a biocompatible, adhesive or thermofusible coating enables the insulation of an electrical part of the microstructure in relation to a mechanical part of the microstructure.

A further aim of the invention is a wafer comprising a series of microstructures formed, preferably, by a collective method, the wafer thus enabling the simultaneous functionalisation of a series of identical pads of microstructures. These identical pads define a family of pads to be functionalised, a wafer being able to comprise different families.

In a first embodiment, this wafer comprises a shared electrode different for each family, this electrode electrically connecting all of the pads belonging to this family of pads.

In a second embodiment, a same shared electrode is used for several families, each family being further characterised by a bare conductive surface (before its lining) of different chemical nature to the sense of the electrografting.

In a third embodiment, the shared electrode is connected to the different pads of a same family via impedances characterising a given family. Said impedances are diodes characterised by a conduction threshold, a zero conduction threshold being by convention attributed to a short circuit. A diode may be used to connect the shared electrode to one or several pads.

The diodes are oriented in such a way as to allow the flow of the electrochemical current during the formation of an organic film on the pads of the family considered. The diode is formed in such a way that its leakage current before the threshold is less than the residual electrochemical current before the formation of the organic film. In a specific embodiment, each pad of a family is associated either with a unique diode, or in a one-to-one manner with a diode of each microstructure.

These embodiments, unique shared electrode, shared electrode for families characterised by the chemical nature of the surface, shared electrode for families characterised by the diodes used, may be combined within a same wafer. In particular, a shared electrode may be used for families characterised in an alternate manner both by the chemical nature of their surface and by the diodes used.

In a specific embodiment of the invention, the shared electrode may be combined with diodes enabling a simultaneous addressing of the pads of a same family, each pad of a microstructure being connected to the shared electrode via a diode making it possible to test separately the microstructures before cutting up the wafer.

The shared electrode may be formed by metallisation at the surface of the wafer. The diodes may be formed by local implantation making it possible to create junctions to semi-conductors of np or pn type.

In a preferred embodiment, the transfer of all of the electrical contacts on a same reference surface plane enables the assembly on a flat support. In this embodiment, the transfer of the contacts on the lower layers may be carried out via metallisations on micromachined inclined faces. In the case of a microstructure formed from surface micromachining of a wafer of SOI, the reference surface plane may be the epitaxied surface.

The microstructure, according to the embodiments of the invention, may be interconnected to a support known as the interconnection support formed on a semi-conductor comprising tracks and different families of electrical interconnection bond pads, of which at least one of the families comprises an adhesive coating formed by electro-initiated grafting.

The patterns of the interconnection support (pads, tracks, sealing joint) are formed by using the selectivity by the materials or by diodes formed by local doping. This local doping is also used for forming the tracks of the support, a suitable polarisation making it possible to ensure the insulation between tracks. In this embodiment, the semi-conductor substrate of the support may be used as the shared electrode.

The microstructure, according to the embodiments of the invention, may be interconnected to a support known as an interconnection support itself comprising an electrical component produced from the assembly of an active electronic part and a functionalisable package cap formed in part as the interconnection support. This latter assembly may be formed at the level of the wafers by known methods (wafer bounding and contact transfer). Preferably, the electrochemical functionalisation of the package cap is carried out after the assembly.

The invention may be used to produce a microsystem comprising one or several microstructures such as described above, assembled on a silicon interconnection support in which one at least of the microstructures is assembled by use of an adhesive coating. In the case of a sensor, the interconnection support has an opening arranged opposite the sensitive surface (in contact with the environment) of the sensor.

Other characteristics and advantages of the invention will become clear from the description that follows, while referring to the appended figures and drawings. This description is given purely by way of indication and is in nowise limitative.

BRIEF DESCRIPTION OF DRAWINGS

FIGS. 3a to 3i represent, in a schematic manner, schematic cross-sections of examples of microstructures according to the invention.

FIG. 5 is a schematic representation of a specific embodiment of a microstructure making it possible to form a pressure sensor according to the invention comprising a functionalised membrane. It comprises a part B representing a cross-sectional view of the microstructure and a part A representing a top view.

FIG. 6 is a schematic representation of a microsystem formed from the assembly on an interconnection support, of a microstructure according to the invention, of a dedicated electronic component (ASIC). It comprises a part A representing a cross-sectional view of the microsystem after assembly, a part B representing a top view before assembly of the interconnection support, and parts C and D schematically representing a top view before assembly of the integrated circuit and the microstructure respectively.

FIG. 7 is a modelling of the configuration allowing the selective functionalisation of two families of pads that are electrically connected. It comprises a part A representing, in a schematic manner, the topology of the configuration and a part B representing an electrical modelling of the part in solution of the electrochemical circuit.

FIG. 8 indicates the modifications to the diagram of FIG. 2 for the electrochemical circuit modelled in FIG. 7.

FIG. 9 is a schematic representation of a specific embodiment of a microstructure according to the invention making it possible to form a pressure sensor comprising a functionalised membrane, electrical contacts covered with an organic film and a sealing joint. It comprises a part A representing a cross-sectional, view of the microstructure and a part B representing a top view.

FIG. 10 describes the diagram associated with the successive steps of functionalisation of the microstructure of FIG. 9.

FIG. 11 is a schematic representation of an interconnection support in silicon comprising a probe enabling a microstructure to be assembled according to the invention and an integrated circuit forming an interfacial electronic component. It comprises a part A representing a cross-sectional view of an interconnection support and a part B representing a top view.

FIG. 12 is a schematic section of a microsystem formed by the assembly of an interconnection support as described in FIG. 11 after functionalisation with a microstructure as described in FIG. 9 after functionalisation and a conventional electronic component assembled by wire-bounding.

FIG. 13 is a schematic representation of an electronic component according to the invention comprising an active electronic part and a protective cover that makes it possible to obtain electrical contacts covered with an adhesive. It comprises a part A representing a cross-sectional view of the component and a part B representing a top view.

FIG. 14 is a schematic section of a microsystem formed by the assembly of an interconnection support in silicon comprising a probe, as described in FIG. 11, after functionalisation, with a microstructure, as described in FIG. 9, after functionalisation, and an electrical component such as described in FIG. 13, after functionalisation.

DETAILED DESCRIPTION OF SPECIFIC EMBODIMENTS

In the following description, identical, similar or equivalent parts on a same figure are annotated by the same reference signs. Furthermore, and in order to ensure the figures are as clear as possible, not all of the elements are represented according to the same scale. Moreover, zones formed in a material or the material constituting said zone are represented by the same reference number.

Electrochemical Circuit and Sensor Substrate

Figure 1:
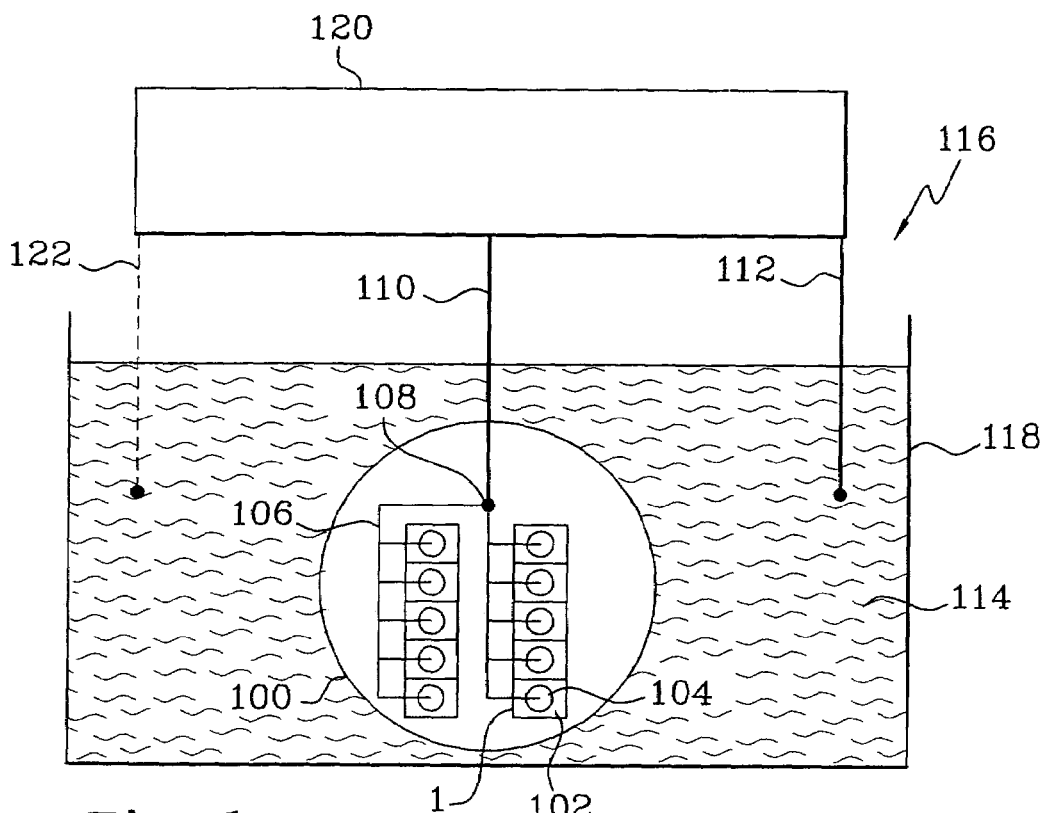
FIG. 1 is a schematic representation of a wafer of silicon comprising a series of micromachined sensors and an electrochemical lining circuit.

FIG. 1 shows a specific wafer of silicon 100, according to the invention.

The wafer of silicon 100 comprises a plurality of microstructures 1 formed on its surface. The microstructures 1 are schematically represented by a mechanical part 102 comprising a deformable zone 104 in the form of a membrane. The microstructures 1 are capable of receiving a lining by electrochemical means making it possible to functionalise their membrane 104. The bare membranes 104 represent pads to be lined. They are electrically connected by a shared electrode 106 to a shared addressing contact represented symbolically by the reference 108 in FIG. 1. The shared addressing contact 108 may be arranged or not on the wafer of silicon 100.

The reference 120 indicates a potentiostat for producing an assembly preferably with 3 electrodes. The potentiostat 120 is connected to a working electrode 110, connected to the shared addressing contact 108, to a reference electrode 122 and to a counter electrode 112. The counter electrode 112, and the conductive pads 104 to be lined are brought into contact with a same electrochemical medium 114 in such a way as to form together with the wafer 100, the electrochemical circuit 116. In the electrode assembly used, the potentials are measured in relation to the reference electrode 122.

One applies a potential to the shared addressing contact 108 either by a 2 electrodes assembly, or, preferably and as represented in FIG. 1, by a 3 electrodes assembly in such a way that said potential is equal to a value V given in relation to a reference.

The composition of the electrochemical bath may be widely variable as a function of the type of lining that one wishes to form on the conductive pads. Lining is understood to mean a thin film organic coating formed by electrochemical means.

Voltammogram

Figure 2:
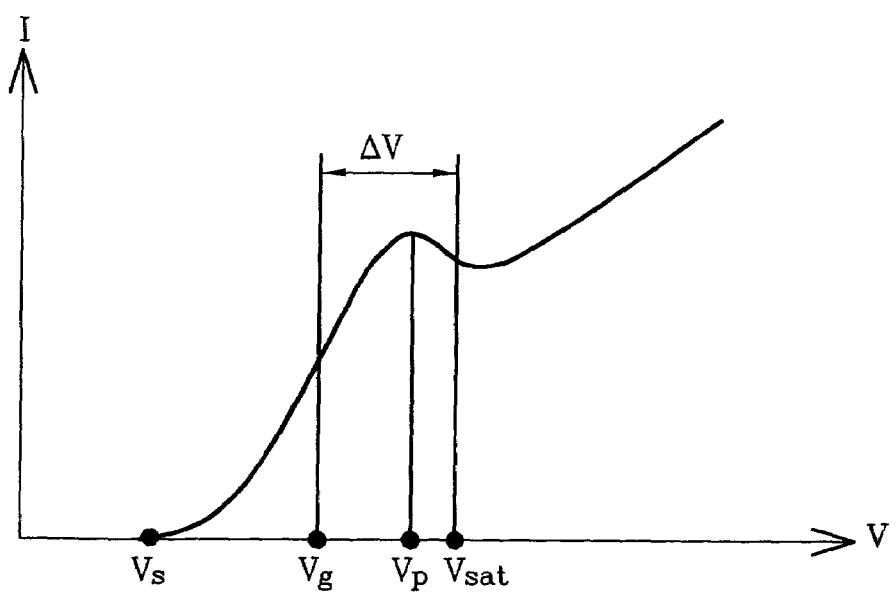
FIG. 2 is a diagram indicating, as a function of a polarisation voltage applied to a conductive pad, the electrochemical current flowing through an electrochemical grafting circuit.

FIG. 2 is a diagram, more precisely a voltammogram, indicating on the Y-axis the evolution of an electrochemical current in the circuit 116 represented in FIG. 1. The current is given as a function of a potential applied to a conductive pad 104 compared to the reference electrode 122. This potential is shown on the X-axis. The current I and voltage V are indicated on an arbitrary scale.

The diagram in FIG. 2, given by way of illustration, corresponds to a specific lining process obtained by electro-initiated reaction: it involves an electrografting coupled to a chemical growth of polymer, such as may be obtained by electro-reduction or electro-oxidation of vinylic monomers or cleavable cyclic monomers by nucleophilic or electrophilic attack, or instead by the electro-reduction or the electro-oxidation of electro-cleavable precursors, in particular when their electro-reduction or electro-oxidation products are reactive radicals, particularly by the electro-reduction of diazonium salts, sulphonium salts, phosphonium salts or iodonium salts. The electrografting of monomers enables polymers to be fixed, in a covalent manner, on the conductive or semi-conductive pads. These polymers "grow" on the surface from the first monomer electro-reduced on the conductive surface 104 through chemical growth. Only the first anchoring step of the first monomer on the surface is electrochemical, the growth being, for its part, purely chemical. It is therefore indeed an electro-initiated reaction. The electrografting of diazonium and analogues salts leads—in general—to layers that do no grow. It is therefore a specific case of an electro-initiated reaction, reduced to its most simple expression.

In the following description, the voltages are given in absolute value, and are implicitly those of the working electrode, measured in relation to a reference electrode. As indicated above, they only correspond to the voltage actually applied experimentally in the case of a 3 electrode assembly (it being assumed that the ohmic drop in the electrochemical circuit is compensated by the potentiostat). In the case of a 2 electrodes assembly, it would have been necessary to impose a voltage V' different from V, not detailed on the graph. The constant polarity of the voltage applied for a given lining is known as the lining polarity. When the polarisation voltage is between a zero value and a starting value Vs, a very weak electric current, even undetectable, flows through the circuit. Whatever the case, this current is insufficient to produce a deposit detectable a posteriori by surface analysis means. One will consider, as a result of this and given the targeted objectives, that the copolymerisation considered here is an electro-initiated reaction that only takes place with a minimum polarisation voltage.

From a starting voltage $V_s$, and up to a lining threshold voltage Vg a weak current flows in the electrochemical circuit 116. However, this current does not necessarily result in a phenomenon of lining. It corresponds to competitive parasite reactions that essentially promote a coupled chemistry that takes place in solution, and therefore do not deliver a significant organic deposition.

Indeed, the electrochemical current flowing in the circuit is not exactly correlated to the growth of a lining material on the conductive pads. The electrochemical current results in at least two separate and competing phenomena. A first phenomenon is the desired phenomenon, corresponding to the formation of the lining on the conductive pads. Another phenomenon corresponds to the parasite formation of polymers in the electrochemical bath, independently of the lining support. The polymers thus formed may attach themselves to the conductive pads by physical sorption but their attachment is not stable, they are eliminated by rinsing.

The actual lining is established from a threshold voltage Vg. One designates by Vsat a potential known as the "saturation potential", which is in general greater than a peak potential Vp for which the current as a function of the applied potential shows a maximum. The "saturation potential" Vsat is a potential from which the thickness of the grafted material does not change with the time of applying the voltage to the conductive pad. Said thickness is the asymptotic limit of the maximum thickness that one may obtain in a given electrolytic bath. This potential also corresponds to a minimum value that makes it possible, from voltametric potential scans carried out between a value less than or equal to Vg and a stopping value greater or equal to this minimum value Vsat, to obtain curves—a curve by stopping value—giving the thickness of the film as a function of the number of cycles, for example under voltametric or multi-slot conditions, the different curves obtained all have this same asymptote, independently of the exact value of the stopping potential used. It is also the minimum potential with which, if one carries out a sufficient number of voltametric cycles between a value less than Vg and a stopping value greater than the saturation potential Vsat, one succeeds in saturating the sites of conductive pads in electrografted polymer chains. In the voltage interval between Vg and Vsat, the lining phenomenon is predominant. This interval is known as the width of the lining potential.

By further increasing the polarisation voltage, beyond Vsat, the lining phenomenon of the conductive pads becomes a minority phenomenon compared to other competing phenomena such as the formation of materials in solution in the electrochemical bath, but the deposition of electrografted polymers at the surface is stabilised.

Thus, the polarisation of the pads to be lined is ideally maintained at least equal to the saturation potential Vsat.

The values of the different potentials, $V_s$, $V_g$ $V_p$ Vsat of the voltammogram depend both on the nature N of the conductive surface of a pad to be lined and on the type of lining X. This will be recalled herein, when necessary, by the notation V[X/N].

Principle of Homogenous Localised Grafting It is difficult to envisage lateral resolutions and in high thickness with electrochemical techniques leading to organic coatings in which the thickness is a function that rapidly rises with the treatment time and the local value of the electric field, which is particularly the case for electro-monitored reactions, such as the electro-deposition of metals or poly-electrolytes, or even electro-polymerisation, for example of precursors of conductive polymers (pyrrole, aniline, thiophenes and derivative thereof). These electro-monitored reactions have in common the ability to provoke the formation of a deposit (not grafted in the case of organic deposits), in which the quantity of material—therefore in general the thickness—is proportional to the charge (temporal integral of the electric current) flowing in the circuit during the protocol. The potential inhomogeneities, caused by ohmic drop differences for example, lead to very different thicknesses. Local electric field inhomogeneities, caused by peak effects, lead to significant fringing effects. This means that the lining extends beyond the implantation conductive pad in a poorly controlled manner in such a way that the spatial resolution of the lining and therefore the density of the conductive pads (ratio between the number of pads each having a surface and the total surface of the substrate on which these pads are situated) is limited.

On the other hand, the electrochemical grafting from electro-initiated reactions such as those described above makes it possible to carry out a localised grafting since it is by nature less sensitive to the electric field inhomogeneities. This localised grafting makes it possible to treat supports with a high density of pads, without using masks.

The local thickness of a coating formed from an electro-initiation reaction using the grafting of insulating monomers to anchor certain organic chains or initiate their growth, depends on the length of the chain forming the molecule of the grafted product and the grafting density. Since the molecule is chosen in such a way that its chain length is an intrinsic factor of the solution used, the method therefore leads to a saturation of the thickness of the coating and limits the fringing effects.

Only the level of covering of the pad by the lining, defined by the ratio between the surface of the covering lining and the surface of the pad, is a function depending on the electrochemical kinetic of the grafting reaction. A first level of homogeneity of the coating is obtained as soon as the potential at the surface of each pad is situated in a window of potential ensuring a minimum grafting kinetic. This condition, less restrictive than that described hereafter, facilitates the practical implementation by limiting the effects of potential inhomogeneities. The level of grafting defined as being the number of grafted surface sites compared to the total number of surface sites available, which is then obtained is typically greater than 30%. This level of grafting corresponds to a covering level of 60%.

When thickness homogeneity is a critical parameter for the quality of the coating obtained, the effects of potential variations may even be avoided by using the method in a saturation mode: by repeating the voltage scanning between a potential less than $V_g$ and a potential that is above the saturation potential up to obtaining a saturation of the number of grafted sites, the thickness of the coating is an intrinsic value that no longer depends on the exact value of the local potential but only on its presence in a window of potential beyond the saturation potential. This mode provides a high level of grafting (greater than 60%, which usually corresponds to the maximum level of grafting, taking account of steric hindrance between neighbouring chains. These levels of grafting assure coverage levels greater than 90%, which signifies that the coating is covering or virtually covering).

Effect of the Access Resistance

The inhomogeneities in the potential may arise from the existence of a resistance of finite value along the shared electrode 106. Indeed, in reference to FIG. 1, the controlled potential is that applied by the potentiostat 120, at the level of the shared addressing contact 108, measured compared to the reference electrode 122. However, it is the potential locally present between each pad 104 to be lined and the reference electrode 122 that governs the electro-initiated reaction.

During the lining phase, the potential V depends on the current flowing in the shared electrode 106. The simplest model that could be used comprises a resistance R that takes account of the potential drop due to the shared electrode 106. In relation to FIG. 1, this involves, for a given pad, the resistance associated with the line length joining this pad to the shared connection point 108. This resistance is variable from one pad to another since the line lengths 106 between the shared addressing point 108 and each of the pads are in general different from each other.

The current $Ic$ flowing through a resistor placed between the point 108 and conductive pad 104 is the sum of the electrochemical currents. It induces a drop in potential $$\delta V = R.Ic$$

This current shows a maximum $Im$ with regard to the peak potential $Vp$ for the domain used. If one assumes that the operator imposes a potential $V=Vsat+\delta Vsat$, then as long as the potential difference ddp $\delta Vsat$ is high compared to the maximum potential drop due to the resistance R, i.e. $\delta Vmax = R.Im$, the voltammogram, therefore the grafting potential zone, is little modified by the presence of the resistance. In other words, as long as $\delta Vmax \leq \delta Vsat$, the potential is everywhere greater than Vsat, and the film deposited by electro-initiated reaction is everywhere of the same thickness, whatever the cartography of the local ohmic drop on the working electrode 110. This condition is met when the value of the resistance in series R is low compared to the differential impedance Rg for treatment of the defined contact, $$Rg=(Vp-Vg)/Im$$

Generally, the resistance R is an equivalent resistance determined from the potential drop along the shared electrode 106 between the conductive pad 104 to be lined and the end of the shared electrode corresponding to the point 108, calculated for the maximum current value Im flowing through it divided by the current necessary to treat the pad. In calculating this resistance R, one must in particular take account of the current effect necessary for the simultaneous treatment of other pads. This resistance R is known as the access resistance or pad electrode resistance.

Furthermore, the maximum electrochemical current Im corresponds to a current density by unit of surface to be grafted. Therefore, it is proportional to the surface of the pad. This current density makes it possible to define by analogy a differential treatment surface resistance characteristic of the electrochemical process used.

A first order of magnitude for the resistance not to be exceeded for the access resistance R may be given by the following approach. The typical value measured for the grafting, of the current density, is around 1 mA/cm2. For pads with sides of 100 µm, this corresponds to a current of 100 nA. The typical width of Vp–Vg is around 300 mV. This gives a differential grafting impedance Rg of around 3 MΩ. For the conductive pads that will be individually supplied by an electrode of resistance R, as long as this resistance R is low compared to this value of 3 MΩ, the ohmic drop due to the shared electrode 106 has no effect on the lining. The generalisation is realised by replacing the resistance R by the electrode resistance of the pad cited above.

First Application to Sensors

For a large number of applications, in particular in the biomedical field, it is necessary to functionalise the surface of a membrane of a microstructure belonging to a sensor, in order to give it for example biocompatibility properties or to limit the cellular adhesion likely to contaminate the sensor. It should be noted that these two functions are not necessarily realised simultaneously because the coating may be considered as biocompatible precisely because it favours cellular colonisation.

For applications requiring a stability in the response of the sensor over the long term, this functionalisation must be carried out from a controlled deposition of thickness that makes it possible to evaluate exactly the effects of the film on the response of the sensor not only at a time t=0 corresponding to the start of the operational life of the sensor but also preferably to any time t of this operational life. The objective is to not lose the benefit provided by the use of a stable electromechanical microstructure, such as for example a membrane 104 in monocrystalline silicon, following the functionalisation by an organic film by nature less stable over time. This is particularly important when the mechanical structure is formed from a mono crystal.

The elasticity of a thin film is a function of the elasticity modulus E of the material and its thickness h. As a first approximation, a coating (2) on an elastic element (1) necessitates a compensation pressure dP given by $$dP = P \times E2/E1 \times (h2/h1)^3$$

dP is by definition the additional pressure to apply at the level of the coating to obtain a pressure P on the elastic element, for example a bare membrane 104 in monocrystalline silicon. The previous equation gives an estimation by default of the effect of the coating since it does not take account of the adhesion between the two materials, the organic material constituting the lining and the elastic material constituting the membrane. By digital simulations, one obtains values closer to reality, which show that this approximate value may be increased by a very variable factor, depending on the case.

One may ideally ask that the presence of the coating does not modify, for a desired pressure sensitivity δP, the response of the sensor. The index of mechanical fluctuation over time of the coating is known as s. For the criterion formulated, $$s = \text{Max}(dP[t] - dP[t=0])/dP[t=0]$$

where dP[t] is the value of the compensation pressure over time, the maximum value being evaluated on the duration of use of the sensor. With this definition, the conditions on the layer are given by $$dP[t=0](1+s) < \delta P \quad (1)$$

A less restrictive condition may be imposed by accepting that the presence of the layer modifies the response of the bare membrane but in -a stable manner over time. This condition assumes a calibration of the sensor after the encapsulation. In this case, the definition of the relative stability of the layer is slightly different $$s = \text{Max}(|dP[t] - dP[t=0]|)/dP[t=0]$$

the presence of the absolute value also makes it possible to take account of the drops in the compensation pressure.

The two definitions agree with each other for low values of s. With this definition, the conditions on the layer are given by $$s \times dP[t=0] < \delta P \quad (2)$$

Thus, for a high precision sensor such as an absolute sensor used in the medical field for measuring physiologic pressure (implanted system), the desired precision δP is around 0.1% (1 mbar on 1 bar).

I.e. dP/P is the variation in relative pressure linked to the presence of the film known as the transmission of the film. The most restrictive condition (1) imposes in this case a transmission less than 0.1%. The second condition (2) allows a transmission between 1 and 5% depending on the value of the index s of mechanical fluctuation of the film over time (from 10% to 50%).

Digital simulations have been carried out for a polymer of elasticity 1 GPa (Parylene) on a silicon membrane of elasticity 200 GPa of 4 μm thickness. For an index of mechanical fluctuation over time of the polymer layer of 10%, the first condition (1) imposes a thickness of the polymer layer less than 1 μm. The second condition (2) makes it possible to use thicknesses up to 3 μm. This thickness of the polymer layer depends slightly on the elasticity of said layer. Further simulations have shown that the thickness of the layer could vary by around ten times the thickness of the membrane for the most flexible materials but must remain less than the thickness of the membrane for materials of intermediate elasticity.

It is important to note that these conditions on the thickness must be able to be assured with a good precision because the elasticity of the layer is a very rapid function of its thickness. Furthermore, the thickness used must be compatible with the function provided by the layer, in particular when it involves a protection function. These two conditions are met with the linings provided by the specific electro-initiated reactions described in this text.

FIGS. 3a to 3i show, in a schematic manner, different embodiments of an electromechanical structure 1 according to the invention.

In FIG. 3a an electromechanical microstructure 1 comprises a first part 102 known as the mechanical part, comprising a zone deformable in an elastic manner 104. The zone 104 is formed in a first conductive material that is deformable in an elastic manner. The zone 104 has a thickness value and an exposed surface 2. A first organic film 4 having a thickness is present on the exposed surface 2 of the deformable zone 104 in first material. According to the invention, the thickness of the first film 4 is such that an elastic response of the deformable zone 104 does not change by more than 5% compared to a response of the zone 104 of the first material alone, or in that the thickness of the first film 4 is less than ten times the thickness of the deformable zone 104.

Preferably the thickness of the first film 4 is such that the elastic response of the deformable zone 104 of the mechanical part 102, equipped with the first film 4, does not change by more than 1% compared to the elastic response of the deformable zone 104 alone.

The first film 4 consists of a layer of a molecule of fixed length bonded, in a covalent manner, to the exposed surface 2 of the deformable zone 104 of the first material, and in a material that may be deposited from an electro-initiated reaction.

The level of covering of the exposed surface 2 by the first film 4 is greater than 60% and preferably greater than 90%.

In the embodiment represented in FIG. 3b, the mechanical part 102 comprises at its surface an annular zone 5, surrounding the exposed surface 2. The annular zone 5 itself comprises a surface 6 and is formed in a second electrically conductive material, different to the sense of the electro-initiated reaction of the first material of the mechanical part 102. A second organic film 7 is present on the surface 6 of said annular zone 5. This second film 7 is a film formed in a material that may be deposited from an electro-initiated chemical reaction.

The embodiment represented in FIG. 3c is a specific embodiment of the embodiment represented in FIG. 3b in which the first conductive material of the deformable zone 104 is a doped semi-conductor. The second conductive material of the annular zone 5 is the same semi-conductor having a doping of type opposite to that of the first material. A junction forming a diode is thus created between the second material of the annular zone 5 and the first material of the deformable zone 104.

The embodiment of FIG. 3d is a specific embodiment in which the electromechanical microstructure 1 comprises a group of first contact pads 8 in a position exterior to the annular zone 5. The group of first pads 8 may only, as represented in FIG. 3d, comprise a single contact 8.

The first contact points 8 may be formed in a third electrically conductive material, different to the sense of the electro-initiated reaction of the first material of the deformable zone 104 and of the second material of the annular zone 5 or different from one only, of these first 104 or second materials 5.

In the embodiment represented in FIG. 3e or 3f, a third organic film 10 is moreover present on the surface 9 of the first contact points 8. This third film 10 is in a material that can be deposited from an electro-initiated reaction.

The embodiments in FIGS. 3e or 3f differ from each other by the fact that in one case the annular surface located underneath the second film 7 is formed in a material 5 different from the first conductive material constituting the deformable zone 104, whereas in the other case the second conductive material located underneath the second film 7 is formed in a material 5 different from the first conductive material by the fact that its doping is of a type different, for example n, for the doping of the first material, for example p, the first and second conductive materials being the same semi-conductors.

In the example represented in FIG. 3g the electromechanical microstructure 1 comprises a second part 11 mechanically integral with and electrically isolated from the first part 102. The second part 11 comprises at the surface one or several second contact pads 12 formed in a material different to the sense of the electro-initiated reaction of the material constituting the second part 11. A fourth organic film 14 is present on the surface 13 of the second contact points 12. Said fourth film 14 is a film formed in a material that may be obtained from an electro-initiated chemical reaction.

In the example represented in FIG. 3h, the electromechanical microstructure 1 comprises a third part 15, electrically insulated from the first part 102, formed in an electrically conductive material. The second part 11 and the third part 15 are electrically connected to each other for example by a liaison 20. A fourth organic film 14 is present on the surface 13 of the second contact points 12. This fourth film 14 is in a material that may be deposited from an electro-initiated reaction.

The example represented in FIG. 3i corresponds to one of the cases represented and described with FIGS. 3a to 3h in which an electrode connection contact 19 is formed in the part 102 in a conductive material different from the first material 102 and is located outside of the exposed surface 2 and of the annular zone 5 if said zone 5 is present. The first material 102 may preferably be for example a doped semi-conductor of a first type and the contact material 19 the same semi-conductor of a type opposite to the first type.

In an embodiment represented in FIG. 9, the mechanical part 102 of the microstructure 1 is in the form of a layer of monocrystalline silicon, lying above an insulating layer 16, for example in silica. The second part 11 is also borne by this same layer of insulating material 16 in such a way that the first 102 and second 11 parts are integral with this insulating layer 16. In this mode, the third part 15 consists of a layer of silicon on which is lying said insulating layer 16. Said insulating layer 16 comprises a recess 18 located immediately under the deformable zone 104. This recess 18 allows the deformable zone 104 layer in monocrystalline silicon 102 to distort. This embodiment of the electromechanical microstructure 1 will be described in a more detailed manner below.

In this embodiment the electromechanical microstructure 1 according to the invention is intended for a medical or veterinary use, and the first organic film 4 is in a material such that the exposed surface 2 of the deformable zone 104 covered with this film 4 has biocompatibility, non-cyctotoxicity and/or anti-adhesion or cellular anti-proliferation functions. The second film 7 is a film having biocompatibility functions and non cyctotoxicity functions.

Before describing the specific embodiment in detail, examples of wafer 100 bearing several microstructures 1 according to one of the embodiments of the invention will be succinctly described in relation to FIGS. 4a to 4f. These figures are intended to illustrate the different ways in which one or several shared electrodes are electrically connected together according to the case of identical parts of the microstructures 1. In order to more clearly illustrate the correspondence with FIGS. 3, the microstructures 1 are represented in cross-sectional view and the path of the shared electrodes is represented as a top view. FIGS. 4a to 4f only comprise two identical microstructures 1, but it must be understood that they normally comprise many more, which are not all necessarily identical. In order to improve the presentation, the reference numbers have been spread out between the two microstructures of each figure.

Figure 4A:
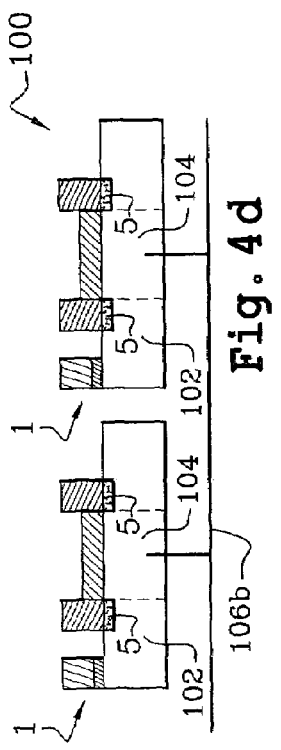
FIGS. 4a to 4f represent different embodiments of a wafer comprising microstructures according to the invention.

In the example represented in FIG. 4a a first shared electrode 106a electrically connects between them all of the mechanical parts 102 formed in the first conductive material. The microstructures 1 may comprise in addition to the deformable zone 104, as represented in FIG. 4a, an annular zone 5 on which is present a second film 7 and a contact pad 8, on which is present a third film 10, as described in relation to FIG. 3.

Figure 4B:
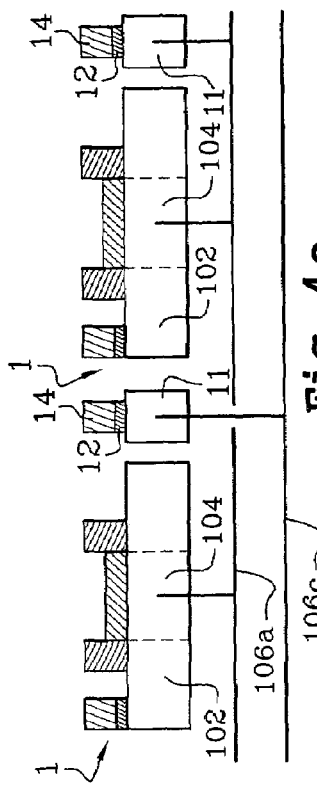
Figure 4C:
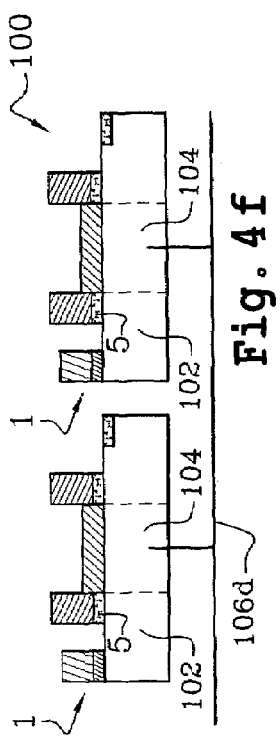

In the examples represented in FIGS. 4b and 4c, the microstructures 1 are respectively the microstructures 1 represented in FIGS. 3c and 3f.

In the example represented in FIG. 4b, the wafer 100 comprises a first shared electrode 106b electrically connecting all of the annular zones 5 between each other. The polarity necessary to electro-initiate the first film 4 corresponds to the open sense of the diode created by the doping in the sense annular zone 5 towards mechanical part 102.

In an embodiment represented in FIG. 4c, the first shared electrode 106a electrically connects all of the mechanical parts 102 between each other. The polarity necessary to electro-initiate the second film 7 corresponds to the open sense of the diode created by the doping in the sense from the mechanical part 102 towards the annular zone 5.

Figure 4D:
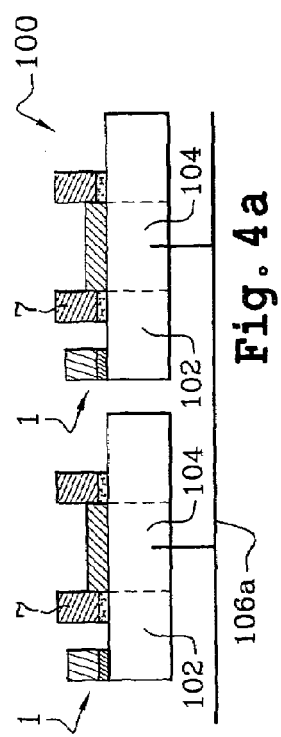

In the example represented FIG. 4*d*, the microstructures 1 are identical to those represented in FIG. 3*f*. A first shared electrode 106*b* electrically connects between them all of the annular zones 5. The polarity necessary to electro-initiate the first 4 and third film 10 is identical and corresponds to the open sense of the diode created by the doping in the sense annular zone 5 towards mechanical part 102.

Figure 4E:
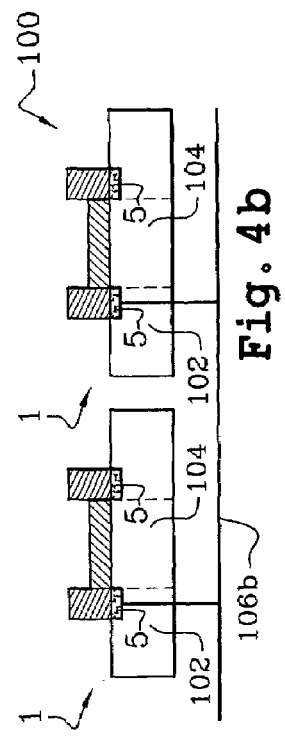

In FIG. 4*e*, the microstructures 1 represented are identical to the microstructures of FIGS. 3*e* or 3*f* but comprise in addition a second part 11 mechanically integral with and electrically insulated from the first part 102. FIG. 4*e* represents uniquely a microstructure identical to the microstructure of FIG. 3*e* but which further comprises a second part 11. The wafer 100 comprises a first shared electrode 106*a* connecting between them all of the first mechanical parts 102. It further comprises a second shared electrode 106*c* connecting between them all of the second parts 11.

Figure 4F:
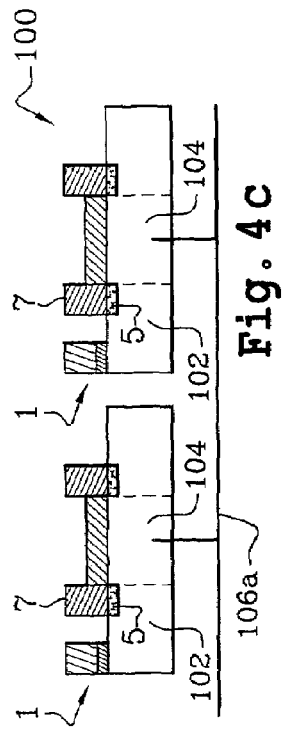

In the example represented in FIG. 4*f*, the wafers 100 comprise a series of microstructures 1 as described in relation to FIG. 3*i* formed at the surface of the wafer by a collective process. The wafer 100 comprises a first shared electrode 106*d* electrically connecting between them all the electrode pads 19. The polarity required to electro-initiate the organic films 4, 7, 10 corresponds to the open sense of the diode created by the doping between the electrode pads 19 and the mechanical parts 102.

FIG. 5 illustrates a specific embodiment of the invention for electromechanical devices requiring a lining. The substrate is a wafer of silicon on which are micromachined electromechanical microstructures 1 intended to be used for forming pressure sensors. FIG. 5 represents just one of these microstructures 1. It comprises a part B representing a cross-sectional view and a part A representing a top view.

The wafer 100 from which is formed the microstructure 1 is an SOI substrate (Silicon On Insulator) consisting of a lower part 15, covered with a layer of silica 16 and a layer of monocrystalline silicon 102 built up by epitaxy, typically of micrometric thickness (upper part of the substrate known as the mechanical part 102). Local etching by chemical means of the layer of silica 16 makes it possible to form a cell under vacuum 18. The imperviousness of the cell 18 after etching is assured by means of a plug 21 that seals an opening formed in the layer of monocrystalline silicon 102 for the etching of the insulating layer 16. The upper part 104 of the cavity 18, consisting of a central part liberated from the layer 102 of monocrystalline silicon, serves as a membrane 104 that distorts under the effect of a pressure. The deformation of the membrane 104 results in a modification of a capacitance value measured between the two planes of silicon 15 and 102 thanks to the electrical contacts 22 and 25 formed by local deposition of gold, on the layer 15 and the layer 102 respectively. To obtain an optimum anchoring between the gold and the silicon, an interfacial layer, typically based on titanium and nickel, is used. In order to improve the electrical contact, an over doping may be formed under the contact points 22, 25. In the following description, a deposit of gold on silicon is taken to mean the use of an intermediate anchoring layer and/or an over doping. The metallisation may also be carried out by any other known metallic deposition.

A lining in the form of a film 4 is deposited on the surface of the membrane 104. By way of example of implementation, with baths containing vinylic monomers and/or cleavable cyclic molecules, one may form in particular coatings, the properties of which may be adjusted. Thus, the electrografting of hydroxy-ethyl methacrylate (HEMA), methyl methacrylate (MMA), butyl methacrylate (BMA), poly ethylene glycol di-methacrylate (PEG-di-MA), N-vinyl pyrrolidone (NVP), and more generally activated vinylic monomers functionalised by substituents (molecular or macromolecular) of biocompatible nature, making it possible to obtain polymers films having good biocompatibility properties, particularly in the sense of the ISO 10993 standard. The films obtained by electrografting are in general insulating, at high grafting levels, but it is not rare to observe that the electrical insulation, particularly in solution, is with all the more reason favoured as the electrografted polymer is more hydrophobic. The deposition of a biocompatible coating 4 on the membrane 104 makes it possible to render the surface in contact with the biocompatible environment (exposed surface), the plug 21 being either a biocompatible material, or covered with a biocompatible non organic material by microelectronic thin film deposition techniques.

In the example represented in FIG. 5, the deformable zone 104 constituting the membrane is substantially circular. The non deformable part of the layer 102 lies on the layer of silica 16. A first excrescence 23 of the layer 102 descends along a gentle slope 318 created by micromachining towards the insulating layer 16.

In order to allow the collective functionalisation of the membranes 104 of all of the mechanical parts 102 present on a same wafer 100, a shared electrode 106*a* such as described in FIG. 1 or FIG. 4 that makes it possible to connect together all of the pads 102 to a shared point 108 on the periphery of the wafer, is formed thanks to a track 106*a* in gold running along the layer of silica 16 on all of the wafer 100. Thus, the reference 24 designates a part of the track 106 crossing from end to end an electromechanical microstructure 1. The track 24 is on each microstructure electrically connected to the layer 102 of this electromechanical microstructure 1 by a gold track 25 lying on the slope 318 created by micromachining of the epitaxied layer 102. These layers are coated with a passivation layer. Interconnection pads 26, 26*a* to an interconnection support 402 that will be described later are opened, according to a known method, in the passivation layer deposited on the Au metallisation.

Selectivity by Material

A first method of depositing a lining on different conductive pads of the electromechanical microstructure 1 using the selectivity by material will now be described.

It has been noted that the different characteristic potentials used for the description of an electro-initiated reaction depend on the nature of the material of the conductive surface. One defines materials of different nature in the sense of an electro-initiated reaction as being materials that differ from each other by, at least for example, one of the following parameters: vacuum electronic output work, [for the french "travail de sortie électronique dans le vide"] solvation of the surface by the electrolysis solvent, Brönsted acidity in the electrolysis solvent.

Thus, for a given lining X, all of the other parameters being equal, the potential Vg[X/Au] necessary to initiate the electro-initiated reaction on the gold is lower than that Vg[X/Si] on the silicon. In practice, successive voltage cycles between the potential necessary to initiate the reaction and a higher potential where the yield of the reaction is optimised, are carried out. The functionalisation of the membrane in silicon from the saturation potential Vsat[X/Si] leads to a higher formation of polymers in solution due to the presence of the surface in gold combined with a lower saturation potential Vsat [X/Au]. This effect may be avoided by successively applying, during a step I the potential Vsat[X/Au] up to saturation of the pads in gold, then during a step II the potential Vsat[X/Si] for the functionalisation of the membranes.

It is also possible to functionalise the surface of the membranes while leaving the electrical contacts of any coating.

During a first lining phase I, a first lining A is applied on the contacts by a potential Vsat[A/Au] allowing the grafting of the lining A on the contacts in gold but not on the membrane in silicon. The typical difference between the two potentials Vsat[X/Au] and Vsat[X/Si] is in fact greater than the typical width of the lining potential (which means that Vsat[X/Au] is less than Vg[X/Si]). The lining A is not grafted on the zones in silicon for the potential Vsat[A/Au].

A second lining B is formed on the surface of the membranes by application of the appropriate potential Vsat [B/Si]. No lining B is formed at the surface of the zones having been functionalised by the lining A even if the potential Vs[B/Au] is less than the applied potential. Indeed, the previously lined pads remain insensitive to the new treatment, particularly when their preliminary lining is insulating: "insulating lining" is here taken to mean a lining that prevents the restarting of an electro-initiated reaction. If this new reaction is for example an electrografting reaction, (i) the non-swelling of the first lining by a solvent of the new reaction; (ii) the insolubility of the monomer of the new reaction in the first lining; (iii) the maximum occupation (maximum level of grafting) of the sites of the conductive pad due to the presence of the first lining; are—independently—causes that could lead to an insulation (in the electrochemical sense) of the pad already lined.

Finally, a selective chemical treatment enabling the lining A to be removed without attacking the lining B is carried out, for example by using a suitable potential protocol in a solvent specific to A. The lining A is used as a molecular mask making it possible to temporarily protect the contacts of the lining operation of the membranes by the lining B. The lining B being for example a film of Poly-HEMA, one may for example mask beforehand certain zones with a film A of 4-nitro phenyl diazonium, said film being then able to be electro-gummed by a very cathodic potential in water.

Requirement for Selectivity

More generally, the use of different linings on certain conductive pads of the front face of the microstructure makes it possible to introduce different additional functions, for example during a preconditioning step carried out in a collective manner simultaneously on all of the sensors, therefore before cutting of the silicon substrate.

For a large number of applications, it is advantageous to be able to introduce other functions to the surface of the microstructure during its preconditioning phase in order to facilitate subsequent assembly phases.

These functions will be more clearly understood from the following example describing one of the possible uses of this type of microstructure as a component of a pressure sensor.

The microstructure may be used within a microsystem as described in [Miniature pressure acquisition microsystem for wireless in vivo measurements, Renard S. et al, presented at the 1st annual international IEEE EMBS Special topic conference on microtechnologies in medicine and biology, October 12–14, in Lyon in France]. Such a microsystem 200 represented in FIG. 6 is formed by assembly:

of an electromechanical microstructure 1 forming the sensitive element of the sensor represented in top view in a schematic manner in FIG. 6 part D, of an ASIC type electronic circuit 400 comprising in particular a digital signal capacitance converter enabling a remote input by magnetic field and a wireless transmission of the measurements.

FIG. 6 further comprises a part A representing a cross-sectional view of the microsystem 200 after assembly and a part B representing a top view before assembly of an interconnection support 402.

THE ASIC 400 processes in particular the data coming from the microstructure 1 and forms an interface between the microstructure 1 and the interconnection support 402. THE ASIC 400 and the microstructure 1 are mounted on the interconnection support 402. The interconnection support 402 comprises a probe 403 coupled to the ASIC 400.

For this use in a measurement microsystem, the microstructure 1 has for example the embodiment described in FIG. 5.

The interconnection support 402 comprises the first connection pads 427 of the ASIC 400 and the second connection pads 426 of the microstructure 1. The firsts connection pads 427 of the support 402 are in geometrical correspondence with the connection pads 427' of THE ASIC, such that the figure formed by the pads of the ASIC may be turned over on the interconnection support 402 so that the pads 427' of the ASIC 400 and the firsts pads 427 of the interconnection support 402 can come into coincidence with each other. In the same way the microstructure 1 is equipped with connection pads 26, 26a shown in FIG. 5 part B and 6 part D by squares on the conductive tracks for example of gold. These pads of the microstructure 1 may come into coincidence after turning over with the second pads of the interconnection support 402. In the assembly represented in FIG. 6 part A, the ASIC 400 and the microstructure 1 are turned over on the interconnection support 402, the connection pads 427' of THE ASIC 400 and those 26, 26a of the microstructure 1 being connected mechanically and electrically for example by a method known as the "flip chip" method to the first and second pads of the interconnection support 402 respectively, by means for example of beads inserted between the pads 427', 26, 26a respectively of the ASIC 400 and of the microstructure 1 and those 427, 426 of the interconnection support 402. External mechanical reinforcement and protection resins 406, 407 are used to terminate the assembly. In an advantageous manner, in the assembled position a crossing opening 405 of the interconnection support 402, is situated opposite the lined membrane 104 of the first film 4. The resin 406 while leaving free access to the membrane 104 through the opening 405, assures in particular an imperviousness and an electrical insulation between the membrane 104 equipped with its film 4 and the remainder of the microsystem 200.

A microsystem 200 as shown in FIG. 6 part A may be used in an autonomous manner for the systems implanted for the spot monitoring of the pressure, in particular in the medical field. In this case the interconnection support 402 is preferably in a biocompatible material (such as polyimide). In the general case, the interconnection support 402 may also serve to place the component 400 in a casing. The size criterion is particularly important for the implanted systems, which excludes the use of conventional encapsulation methods.

After the membrane 104, a second type of functionalisation concerns therefore the surface of the interconnection: bond pads 26 electrically connected to the membrane 104 and 26a electrically connected to the lower silicon plane 15 (FIG. 5 part A). A particularly suitable known method consists in assembling as described above in relation to FIG. 6, the microstructure 1 after cutting "front face turned over"

towards the interconnection support 402 (method known as "flip-chip") by using fusible beads for the electrical and mechanical interconnection. In this case, the interconnection bond pads 26, 26a are opened, according to a known method, in a passivation layer deposited on the Au metallisation. The beads may be obtained after annealing of a deposit formed from different known techniques.

It is also interesting to be able to form this function from a conductive polymer coating deposited as a thin film ("flip-chip polymer").

In this "flip chip" assembly mode of a microstructure 1, the support 402 further comprises a window 405 opposite the membrane 104 of the microstructure 1 to allow a direct contact towards a medium to be characterised, necessary for the measurement of pressure. The insulation between the contacts and the medium, which is necessary for the correct operation of a sensor incorporating the microstructure 1, must be achieved by a sealing joint (at the level of the annular zone surrounding the exposed surface).

Said joint may be formed from known techniques as explained in relation to FIG. 6, making it possible to diffuse by capillarity a resin 406 between the support 402 and the microstructure 1 (known as the "underfill" technique) coupled to the capillarity effect so that the resin does not cover the membrane 104 equipped with the film 4.

It is also interesting to aim to form this joint from an insulting polymer. This corresponds to a third functionalisation requirement.

The different functionalisations described require polymers having different properties: restriction on the thickness and chemical type functionalisation for the membrane 104 of the microstructure 102, conductivity and adhesion property for the electrical contacts 410–413 and insulation and adhesion property for the annular zone to form a sealing joint.

It is possible to use the selectivity arising from the material to arrange for a first means of selectivity when the two pads to be lined are or may be electrically connected, for example by using a deposit of gold on the surface of silicon as described above. Another means of selectivity may be used in the general case.

Effect of a Diode

A selective addressing is used when it is necessary to graft different polymers on surfaces of the same chemical nature from a same shared electrode. This choice of a shared unique electrode may be a choice to simplify the electrode network when the component is manufactured in a collective manner on a wafer or may be imposed by the manufacturing technology.

FIG. 7 illustrates a circuit equivalent to the configuration used in the case of two distinct families of pads using a same electrode. The part A of the figure represents the topology of the configuration. At the surface of a component 500 included in a wafer 514 comprising several of them, are located two types of pads 502 and 504 of the same chemical nature, for example gold. The two sets of pads of type 502 and 504 respectively form the families 510 and 512 when the component 500 is repeated on the wafer 514. The pads 502 of the family 510 are connected to a shared electrode 506 running along the wafer. The selective addressing is obtained by locally intercalating diodes 508 between the pads 504 of the family 512 to be lined and the shared electrode 506. The part B of FIG. 7 is an electric modelling of a part of the electrochemical circuit.

During the grafting operation, the potential V existing between a conductive pad 504 to be lined and the reference depends on the current flowing in the addressing circuit.

FIG. 8 is the voltammogram associated with the configuration described in FIG. 7. It is established as a function of a voltage Vr measured by a voltmeter between the source and the reference electrode, not represented on the diagram, in a conventional three electrode assembly (cf. FIG. 1).

The voltammogram comprises two curves 600 and 602 associated respectively with the lining of the pads of the families 510 and 512 for a given lining. The curve 600 is identical to that represented in FIG. 2 since the potential present on the pad 502 is identical to that applied at the level of the source 506. This model does not take account of the possible existence of a resistance along the shared electrode considered as negligible according to the conditions described previously. The curve 602 is, for its part, different due to the existence of the diode 508 between the pad 504 and the source 516: the potential present on the pad 504 is not that applied by the source 506.

In order to model the effect of the diode intercalated between the shared electrode and a conductive pad, it is necessary to return to the electrical model proposed in FIG. 7 by examining the transitory effects corresponding to the establishment of the potential.

In a simple model, the electrochemical reaction as described by the voltammogram of FIG. 2, may be modelled by a diode 518 of threshold Vs combined with a resistor in series Rg 520 making it possible to take account of the slope of the voltammogram. The diode 508 used as shift means may be modelled by a perfect diode 522 combined with a resistor 524 in parallel Rd making it possible to take account of the leak currents. The model assumes that the electrochemical current before the threshold Vs is less than the leakage current of the intercalated diode. If the diode is oriented in the closed sense for the voltage polarity used, the threshold is considered as infinite.

From an initial situation where all of the potentials are zero, the increase in the potential Vr applied at the level of the electrode 506 results in the appearance of a weak leakage current through the resistor Rg making it possible to electrically charge the conductive pad 504: the potential V at the level of the conductive pad 504 is equal to the potential Vr. As long as these potentials remain below the threshold Vs, there is no electrochemical reaction. When the potentials V and Vr reach the value Vs, there is the appearance of a first electrochemical current arising mainly from the chemistry in solution. This current creates a shift between Vr and V arising from the resistor Rd. The potential V at the level of the conductive pad is therefore less than the potential Vr applied by the source. This difference has an asymptotic value Vd, which corresponds to the conduction threshold of the diode.

One therefore observes that the new curve 602 is shifted, and more precisely translated from a value δV towards high voltage values. This shift is equal to Vd, the conduction threshold of the diode, for currents higher than the leakage current of the diode. If the leakage current of the diode is less than the maximum electrochemical current before the grafting starts, the grafting threshold Vg for the family 512 is shifted by the value of the conduction threshold of the diode.

In conclusion, in an electrochemical bath containing a given lining material, it is therefore possible to selectively allow the lining of certain pads not provided with diode type shift means or provided with shift means of low amplitude, while at the same time preventing the lining of other pads associated with shift means of greater amplitude. The amplitude of the shift is linked to the conduction threshold of the diodes. The application of an identical voltage Vr by the source will result in different local voltages V triggering or not triggering the lining according to the choice of the polarisation maximum.

For example, for the example illustrated in FIGS. 7 and 8, let us assume that the families of pad 510 and 512 must respectively receive linings A and B. The diode is oriented in such a way as to be open for the sign of potential used to trigger the lining B. The threshold potential of the diode is chosen greater than the width of the lining potential of A on Au. An applied voltage of maximum value Vsat[A/Au] will allow the lining of the first family of pads 510 but will not be sufficient for the lining of the second group of pads 512.

If the following electrochemical bath B is different, the lining threshold Vg[B/Au] may be lower or higher than those of the first bath. A lining of the still unlined conductive pads may take place under the application of a maximum polarisation voltage Vsat[B/Au]+Vd, Vd being of finite value by the choice of the orientation of the diode.

The association of different lining pads with different means of threshold selection, with different thresholds, therefore makes it possible to distinguish different families of conductive pads that may be lined selectively.

Implementation for Sensors

FIG. 9 represents an example of an embodiment of a microstructure 1 that could be used in a pressure sensor that could receive three different functionalisations at its surface. It is formed as for that described in FIG. 5 from an SOI substrate but comprises supplementary functions enabling a multiple functionalisation.

Three types of functions may be introduced on the upper face of the microstructure by grafting of polymers:
  the functionalisation of the membrane 104 such as on the microstructure described in relation to FIG. 5, for example to ensure the non cyctotoxicity and the cellular anti-adhesion in the form of a first film 4,
  the formation of a sealing joint that makes it possible to ensure the electrical insulation between the contacts 8, 12 and the zone of the membrane 104 after the assembly of the sensor on an interconnection support 402 in the form of a second film 7,
  the functionalisation of the contacts 8, and 12 for the electrical connection by flip-chip in the form of films 10 and 14 respectively.

The contacts 8 and 12 make it possible to electrically reach respectively the membrane 104 and the lower part 15 of the substrate (fixed part of the capacitance formed between the membrane 104 and the lower layer of silicon 15). The detection of the deformation is realised by measuring the capacitance variation between these two contacts. Other types of microstructures included in deformation pressure sensors exist such as piezoresistive sensors which could necessitate the same type of functionalisation. In order to ensure perfect planeness between the two contacts 8, 12 which facilitates the subsequent assembly, the contact 12 is formed on a contact formed on the same layer of silicon 102 as the membrane 104 but insulated from it by an etching 28 of the upper layer of silicon 102. An inclined face 710 micromachined at the end of the upper layers 102 in monocrystalline silicon and the insulating layer 16 on which lies the layer 102, makes it possible to ensure the connection between the lower layer of silicon 15 and the pads 12 by simple metallisation of a track 20 on the surface. An electrode 106c at the level of the lower layer 15 of the substrate makes it possible to address all of the contacts 12.

In the chosen example, the upper part 102 of the microstructure 1 is of type p. A local n type implantation 5 is formed at the surface of the layer 102. This implantation 5 covers an inclined plane 318 formed as described in relation to FIG. 5, situated in a diametrically opposite manner to the face 710 in relation to the membrane 104, and covers an annular zone of the layer 102 surrounding said membrane 104. The implantation 5 around the membrane 104 defines an annular zone for the formation of a sealing joint at its surface. A shared electrode 106b formed by evaporation of a layer of gold on the insulating layer 16 in silica electrically and mechanically separating the conductive layers in silicon 102 and 15 makes it possible to electrically connect all of the implantations 5 to a shared polarisation source.

In this implementation, the shared electrode 106b makes it possible to address the implantation 5 by the intermediary of a contact in gold 29 covering a part of the inclined plane 318 and, via a diode formed from the np junction, the surface in silicon of the membrane 104 and finally the contact in gold 8 through the diode and the layer 102. The junction np is a diode that is open for negative polarisations. The inversion of the dopings enables a diode to be obtained that is open in the opposite sense.

Selective Grafting on the Microstructure

FIG. 10 describes on a voltammogram the cycles carried out to provide the different linings to the microstructure as described in FIG. 9.

For a given lining X, there exists three current curves as a function of the potential applied at the level of the source via the electrode 106b.

The curve 800 describes the voltammogram for the grafting of X on the contact pad 8. It is associated with potentials Vg(X/Au) and Vsat(X/Au) shifted from the threshold voltage Vd of the diode i.e. Vg(X/Au)+Vd and Vsat(X/Au)+Vd marked 801 on the curve. The curve 802 describes the voltammogram for the grafting of X on the annular zone 5 to form the sealing joint in the form of the second film 7. This grafting is associated with the potentials Vg(X/Si) and Vsat(X/Si) marked 803 on the curve. The curve 804 describes the voltammogram for the grafting of X on the membrane 104. It is associated with the potentials Vg(X/Si) and Vsat(X/Si), shifted by the diode threshold, i.e. Vg(X/Si)+Vd and Vsat(X/Si)+Vd marked 805 on the curve.

The first lining A in the form of a film 10 is formed on all of the contact points 8 by polarising the shared electrode 106b to the potential 801 Vsat(A/Au)+Vd. This potential is not sufficient to trigger the lining by A of the implanted zones 5 in silicon because V(X/Au)+Vd is less than V(X/Si). The linings of the membranes 104 in silicon are also out of reach for all the more reason due to the presence of the diode.

The second lining B is formed on all of the implanted zones 5 in the form of a film 7 forming impervious joints 7 by taking the shared electrode 106b to the potential 803 Vsat(B/Si). The membrane 104 is not lined due to the presence of the diode. The contact pad 8 is not affected by the operation because it has been saturated by the lining A.

The third lining C in the form of the first film 4 is formed on all of the membranes 104 by taking the shared electrode 106b to the potential 805 Vsat(C/Si)+Vd corresponding to the potential necessary for the lining C on the silicon increased by the diode threshold cited above. The annular zone 5 as well as the contact points 8 are not affected by the operation.

During these three operations, the other shared electrode 106c is maintained at a zero potential. The lining of the contacts 12 is carried out separately from a lining A. It can also be carried out simultaneously with the deposition of the first lining A by using a supplementary source enabling the second shared electrode 106c to be taken to the potential Vsat(A/Au).

For the formation of a given lining, the polarity of the generator is determined by the nature of the monomers in solution. It is this that determines the choice of the orientation of the diode 508 (FIG. 7) formed by the junction np in such a way that this is polarised in the open sense so that an electrochemical current can flow once the conduction threshold of the diode 508 is exceeded. Therefore, it is necessary that the linings A and C are associated with potentials of same polarity.

The lining A corresponds for example to a layer of PBMA doped with silver salts, of around 0.5 µm thickness.

The lining B corresponds for example to a layer of Poly Butyl-MethAcrylate (PBMA).

The lining C corresponds for example to a layer of poly-(PEG-dimethacrylate) of around 0.5 µm thickness.

These layers are formed in baths of butyl methacrylate and PEG dimethacrylate, respectively, in dimethyl formamide (DMF) in the presence of tetraethyl ammonium perchlorate as electrolyte support. These three linings are associated with negative polarities, which is coherent with the implantation example given for the microstructure 1 in FIG. 9.

Possibility of Testing the Microstructures

In order to avoid resorting to implantations of the layer 102, one may also form the annular conductive zone 5 around the membrane 104 by deposition of a layer of another electrically conductive material (such as for example copper) different, in the sense of an electro-initiated reaction, from the gold and the silicon used for the contacts 8 and the membrane 104 respectively, in order to selectively obtain the three different functionalisations.

The configuration describes in relation to FIG. 9 when the doping is not used to form the annular zone or the configuration of FIG. 5 makes it difficult to test the microstructures 1 before cutting of the wafer 100: this test can only be carried out if the upper layers 102 of microstructures 1 are electrically insulated from each other, the lower parties 15 being by construction connected between themselves on a wafer 100.

The following implementation enables this requirement to be met. The connection of the different upper layers 102 of the microstructures 1 to the shared electrode 106b is achieved via the contact known as the electrode contact 29 formed on a doping implantation 5 of type opposite to that of the upper part 102. The diode thus created is chosen in such a way as to be on during the different lining operations. The configuration of FIG. 9 directly has this property, since the contact 29 may be considered as an electrode contact.

Thus, for these different configurations comprising an electrode contact 29, during a test phase, one uses an electrical configuration that makes it possible to maintain between the shared electrode 106b for the configuration FIG. 9 and the membranes 104 a reverse voltage that makes it possible to close the diodes. The closing of the diodes then has the effect of electrically insulating the different membranes 104 from one structure to the other.

In a practical manner, the test of the different microstructures 1 present on the wafer 100 is carried out from an external measurement circuit comprising different measurement or supply points intended to be connected to the contacts 8 and 12 each connected respectively to an armature of a capacitance formed between the upper layers 102 and the lower layer 15. The contact 8 is connected to the armature 102 and the contact 12 to the armature formed by the part of the layer 15 opposite the layer 102. The voltages are measured by comparison to the chosen voltage in the external circuit. An additional voltage, known as the polarisation voltage, chosen in absolute value greater than or equal to all of the other voltages used, is applied on the electrode 106b or more generally on the electrode contact 29. Its sign is opposite to that used for the lining operation: it therefore makes it possible to close the different diodes 508. In this configuration, no current flows between the pads by the intermediary of the polarisation circuit: the component is functional and may be tested or used normally. The application of test voltages may take place by the intermediary of a test shoe.

In conclusion, the implantations may therefore be used even on the configuration of the microstructure described in FIG. 5 or when, in a more general manner, the selectivity by the materials is used, to allow the testing of the microstructures before cutting of the wafer.

Implementation for an Interconnection Substrate

FIG. 11 describes an interconnection substrate 402 that could be used for the individual mechanical and electrical assembly of a microstructure 1 as described in FIG. 9. The part A represents a cross-sectional view of the support and the part B a top view.

The example given corresponds to a support functionally identical to the support used to form a pressure measurement microsystem as described in FIG. 6. This support is formed in a collective manner on a wafer of silicon 900 of type n that makes it possible to ensure a typical minimum conductivity of 10 $\Omega$.cm. This wafer may be thinned according to known techniques that make it possible to obtain a typical thickness of less than 100 µm. The probe 902 is formed by deposition of a layer of gold insulated from the principal substrate 900 by a layer of silica 904. Four contact points 906 are used to connect an ASIC 400 for example such as described in FIG. 6. The pads 908 are used for the electrical connection with the pads 8, 12 of the microstructure 1 as represented in FIG. 9. These pads 908, 906 are formed on p type local implantations 910 also marking out the electrical tracks of the support 402. A contact 916 is directly connected to the substrate 900 with intercalary doping. The support comprises a circular recess 405 obtained by a machining.

In this configuration, the conductive substrate 900 is used as shared electrode. The underneath of the substrate 900 comprises a metallic deposit 918 making it possible to homogenise the resistance of the shared electrode if the conductivity of the substrate 900 is not sufficient. The functionalisation of the support 402 by electrografting is carried out at least in three steps for depositing the linings A' and B' complementary to those used for the microstructure 1 represented in FIG. 9.

In a first step, the potential applied makes it possible to functionalise the contact 916 with a lining A'. The non-doped part of the upper face of the substrate 900 is not affected because the silicon requires a higher potential. The doped part 910 and the contacts 906 and 908 are moreover protected by the diode between the substrate 900 and the implanted part 910.

In a second step, a lining A' is formed on the contacts 908 and 916. This step requires a higher potential due to the diode. The non-doped part of the upper face of the substrate 900 is not affected because the grafting on silicon requires a higher potential than the grafting potential on the gold increased by the diode shift.

In a third step, the potential applied makes it possible to functionalise the remainder of the upper face of the substrate 900 with a lining B'. The doped part 910 and the contacts 906 and 908 are protected by the diode.

The orientation of the diodes is determined by the polarity of the lining A'. In our example, this polarity is negative. It is possible during a fourth step to cover the doped zones 910 to finish the insulation of the support. In our example, A' is chosen identical to A and B' identical to B.

The contact 916 is used to positively polarise, in the example given, the substrate from a voltage supplied by the ASIC 400. This voltage, for example the maximum supply voltage used in the electronic component 400 for the polarisation of the transistors, makes it possible to ensure the electrical insulation between the different contacts 906 and 908 during operation of the microsystem. It has been verified that the presence of additional diodes does not modify the functionality of the microsystem as described above, including in the transitory phases.

The ASIC 400 can also, when the compatibility of the technologies so allows, be directly formed on the layer 900 of the support 402 in order to avoid a supplementary interconnection.

Product Obtained

FIG. 12 is a schematic section of a microsystem 200 formed by the assembly of a support 402 as described in FIG. 11 after functionalisation with a microstructure 1 as described in FIG. 9 after functionalisation and a traditional electronic component 400 assembled by wire-bounding.

THE ASIC 400 is connected to the support 402 by gold wires 1010 thermowelded (traditional wire-bounding) as indicated in the figure. This operation may also be carried out by conventional flip-chip. The microstructure 1 is assembled on the support 402 by slight compression and heating in order to allow thermofusion of the linings opposite. The assembly is carried out via the linings 10, 14 of contacts 8, 12 respectively of the microstructure 1 and the corresponding linings of the support deposited on the pads 908. This makes it possible to establish the electrical contacts in 1006. The assembly is also achieved via the lining 7 of the annular zone 5 of the microstructure 1 and the corresponding lining of the substrate 900 of the support 402 around the opening 405. This makes it possible to establish a sealing joint in 1008. The rear face of the component is impregnated in a resin 1012. One may verify that in this configuration, the electrical part of the microsystem is effectively insulated from the surrounding medium whereas the membrane 104 of the microstructure 1 is in contact with this latter element via the lining 4.

Method for Assembling an ASIC

In order to ensure the homogeneity of the method, it may be advantageous to use the same electrical interconnection technique for the ASIC 400 associated with the microstructure 1 of a microsystem. Due to the surface roughness of such a component, it is difficult to use a standard component without supplementary surface treatment operations for preparing the assembly. FIG. 13 describes another approached based on known "chip size package" technologies. These technologies use an intermediate wafer 1100 bonded to an active wafer 1102 comprising the ASICs 400 by waferbounding to provide a new layer interfacing with the exterior. The first known objective of the use of such a technique is to transform contact points 1104 of small size into standard pads 1110 and to provide an integrated casing. Different known solutions exist to make this type of component. The reference 7 describes for example how to form in a collective manner the silicon package cap 1100 above the component 1102 by transferring the contacts 1104 of component to the surface of the package cap in 1110.

It is possible to graft the linings necessary for the assembly of the component on this second wafer 1100 by using the same principles as those described for the interconnection support 402. The shared electrode is formed by the substrate 1100 and local implantations 1108 making it possible to assure the insulation between contacts 1110 when the substrate is taken to the suitable potential by the intermediary of the contact 1112. For reasons of temperature resistance, it is preferable to carry out the treatment after the assembly of two wafers 1102 and 1100.

The interest of this implementation is then to provide an alternative solution for the ASIC 400 to the assembly by fusible beads, of easy implementation (low assembly temperature, no problem of cleaning the surface after the operation, in particular to eliminate the flux present in the fusible beads, etc.) and making it possible to increase the density of contacts.

Product Obtained

FIG. 14 is a schematic cross-section of a microsystem 200 formed by the assembly of an interconnection support 402, as described in FIG. 11, after functionalisation, with a microstructure 1, as described in FIG. 9, after functionalisation, and a ASIC 400 as described in FIG. 13, after functionalisation.

The assembly of the microstructure 1 on the interconnection support 402 is identical to what has been described in relation to FIG. 12. The assembly of the ASIC 400 as represented in FIG. 13 is formed by the intermediary of the lining deposited on the pads 1110 of the ASIC 400 and the lining deposited on the pads 906 of the support 402 arranged opposite each other. The lining respectively of the pads of the ASIC 400 and the support pads 402 are of the thermofusible conductive type A and A'.

CITED DOCUMENTS

[1] Development of a completely encapsulated intraocular pressure sensor, Walter P. et al, Ophthalmic Research (2000), 32, p 278–284.

[2] Microfluidic plastic capillaries on silicon substrates: a new inexpensive technology for bioanalysis chips, P. F. Man et al, presented at the MEMS 1997 Conference, Jan. 26–30 1997, Nagoya, Japan.

[3] Delamarche E., Michel B., Gerber Ch., Langmuir (1994), 10, p 2869 and

[4] Kumar A., Whitesides G. M., Applied Physics Letters (2002), 63, p 1993

[5] WO 0057467

[5] U.S. Pat. No. 6,137,183

[6] Miniature pressure acquisition microsystem for wireless in vivo measurements, Renard S. et al, presented at the 1st annual international IEEE EMBS Special topic conference on microtechnologies in medicine and biology, October 12–14, in Lyon in France

[7] FR 97014608

The invention claimed is:

1. An electromechanical microstructure comprising:
   a first mechanical part formed in a first electrically conductive material, and which comprises (1) a zone deformable in an elastic manner having a thickness value and an exposed surface and (2) a first organic film having a thickness, present on a whole of the exposed surface of the deformable zone, wherein the first organic film is bonded in a covalent manner to the exposed surface of the deformable zone and formed from an electro-initiated reaction;

an annular zone at a surface of the first mechanical part, surrounding the exposed surface, having itself a surface and formed in a second electrically conductive material, different in a sense of the electro-initiated reaction from the first electrically conductive material of the first mechanical part; and a second organic film present on the surface of the annular zone, the second organic film formed in a material that may be deposited from an electro-initiated chemical reaction.

2. The electromechanical microstructure according to claim 1, wherein the thickness of the first organic film is such that elastic response of the deformable zone equipped with the first organic film does not change by more than 5% compared to a response of a bare deformable zone, or wherein the thickness of the first organic film is less than ten times a thickness of the deformable zone.

3. The electromechanical microstructure according to claim 2, wherein the thickness of the first organic film is such that elastic response of the deformable zone equipped with the first organic film does not change by more than 1%.

4. The electromechanical microstructure according to claim 2, wherein a level of cover of the exposed surface by the first organic film is greater than 60%.

5. The electromechanical microstructure according to claim 2, wherein the first electrically conductive material constituting the first mechanical part is a doped semiconductor, the annular zone is formed in a second material formed by doping of type opposite to that of the first material.

6. The electromechanical microstructure according to claim 1, wherein the first mechanical part comprises one or plural contact points in a position exterior to the annular zone.

7. The electromechanical microstructure according to claim 1, wherein the first mechanical part comprises one or plural first contact points having a surface formed in a third electrically conductive material, different in a sense of the electro-initiated reaction from the first electrically conductive material, in a position exterior to the annular zone, and wherein a third organic film is present on the surface of the first contact points, the third organic film formed in a material that may be deposited from an electro-initiated chemical reaction.

8. The electromechanical microstructure according to claim 7, further comprising a second part, electrically insulated from and mechanically integral with the first mechanical part comprising one or plural second contact points having a surface formed in a material different in the sense of the electro-initiated reaction from a material constituting the second part, and wherein a fourth organic film is present on the surface of the second contact points, the fourth organic film formed in a material that may be deposited from an electro-initiated chemical reaction.

9. The electromechanical microstructure according to claim 8, further comprising a third part, mechanically integral with the first mechanical part and the second part, electrically insulated from the first mechanical part, formed in an electrically conductive material, and wherein the second part and the third part are electrically connected.

10. The electromechanical microstructure according to claim 9, wherein the mechanical first part includes a first layer of monocrystalline silicon, and wherein the first mechanical part and second part are integral with a same insulating layer, and wherein the third part includes a second layer of silicon on which lies the insulating layer.

11. The electromechanical microstructure according to claim 10, wherein the insulating layer comprises a recess situated immediately underneath the deformable zone.

12. A wafer comprising a series of the electromechanical microstructures according to claim 9, and comprising a first shared electrode electrically connecting all of the first mechanical parts of the series of the electromechanical microstructures and a second shared electrode formed on the surface of the wafer electrically connected to the second mechanical part.

13. A wafer comprising a series of the electromechanical microstructures according to claim 8, and comprising a first shared electrode electrically connecting all of the first mechanical parts of the series of the electromechanical microstructures and a second shared electrode formed on the surface of the wafer electrically connected to the second mechanical part.

14. The electromechanical microstructure according to claim 7, wherein the first electrically conductive material constituting the first mechanical part is a doped semiconductor, and wherein a doping of type opposite to that of the first material defines an electrode contact at a surface of the first mechanical part outside of the exposed surface.

15. The electromechanical microstructure according to claim 7, wherein the second organic film is a film with biocompatibility and non-cyctotoxicity functions.

16. A pressure sensor incorporating the electromechanical microstructure according to claim 15.

17. A wafer comprising a series of the electromechanical microstructures according to claim 7, and comprising a first shared electrode electrically connecting all of the first mechanical parts of the series of the electromechanical microstructures.

18. A microsystem comprising the electromechanical microstructure according to claim 7, electrically assembled with a front face turned round on an interconnection support comprising an opening leading out opposite the deformable zone of the microstructure, a film of the annular zone of the microstructure being in an insulating thermofusible material and coming into contact with a substrate of the support to form a sealing joint around the deformable zone of the microstructure, the film of contact points of the microstructure being in a conductive thermofusible material and coming into contact with pads of the support to form a mechanical and electrical connection between the microstructure and the support.

19. A The microsystem according to claim 18, wherein contact points of the support comprise a film formed in a conductive thermofusible material obtained from an electro-initiated reaction, the pads coming into contact with films of the contact points of the microstructure to ensure an electrical and mechanical connection between the support and the microstructure by heat sealing.

20. The electromechanical microstructure according to claim 2, wherein the first organic film is in a material such that the exposed surface of the deformable zone covered with this film has biocompatibility, non cyctotoxicity, and/or anti-adhesion or cellular anti-proliferation functions.

21. The electromechanical microstructure according to claim 1, wherein the thickness of the first organic film is such that elastic response of the deformable zone equipped with the first organic film does not change by more than 1%.

22. The electromechanical microstructure according to claim 21, wherein the first organic film includes a layer of a molecule of fixed length.

23. The electromechanical microstructure according to claim 1, wherein a level of cover of the exposed surface by the first organic film is greater than 60%.

24. The electromechanical microstructure according to claim 23, wherein a level of cover of the exposed surface by the first organic film is greater than 90%.

25. The electromechanical microstructure according to claim 1, wherein the first electrically conductive material constituting the first mechanical part is a doped semiconductor, the annular zone is formed in a second material formed by doping of type opposite to that of the first material.

26. The electromechanical microstructure according to claim 25, wherein the first mechanical part comprises one or plural first contact points having a surface formed in a third electrically conductive material, different in a sense of the electro-initiated reaction from the first and second electrically conductive materials, in a position exterior to the annular zone, and wherein a third organic film is present on the surface of the first contact points, the third organic film formed in a material that may be deposited from an electro-initiated chemical reaction.

27. The electromechanical microstructure according to claim 26, further comprising a second part, electrically insulated from and mechanically integral with the first mechanical part comprising one or plural second contact points having a surface formed in a material different in the sense of the electro-initiated reaction from a material constituting the second part, and wherein a fourth organic film is present on the surface of the second contact points, the fourth organic film formed in a material that may be deposited from an electro-initiated chemical reaction.

28. The electromechanical microstructure according to claim 27, wherein the first mechanical part includes a first layer of silicon, and wherein the first mechanical part and second part are integral with a same insulating layer.

29. The electromechanical microstructure according to claim 28, wherein the insulating layer comprises a recess situated immediately underneath the deformable zone.

30. A wafer comprising a series of the electromechanical microstructures according to claim 26, and comprising a first shared electrode electrically connecting all of the first mechanical parts of the series of the electromechanical microstructures, and wherein a polarity necessary to electro-initiate the second organic film corresponds to an open sense of a diode created by the doping in a sense from the deformable zone towards the annular zone of the first mechanical part.

31. A wafer comprising a series of the electromechanical microstructures according to claim 26, and comprising a first shared electrode electrically connecting all of the annular zones between them, and wherein a polarity necessary to electro-initiate the first and third organic films is identical and corresponds to an open sense of a diode created by the doping in a sense annular zone to the deformable zone of the first mechanical part.

32. A wafer comprising a series of the electromechanical microstructures according to claim 25, and comprising a first shared electrode electrically connecting all of the annular zones between them, and wherein a polarity necessary to electro-initiate the first organic film corresponds to an open sense of a diode created by the doping in a sense annular zone towards the deformable zone of the first mechanical part.

33. A wafer comprising a series of the electromechanical microstructures according to claim 25, and comprising a first shared electrode electrically connecting all of the first mechanical parts of the series of the electromechanical microstructures, and wherein a polarity necessary to electro-initiate the second organic film corresponds to an open sense of a diode created by the doping in a sense from the deformable zone towards the annular zone of the first mechanical part.

34. The electromechanical microstructure according to claim 1, wherein the first electrically conductive material constituting the first mechanical part is a doped semiconductor, and wherein a doping of type opposite to that of the first material defines an electrode contact at a surface of the first mechanical part outside of the exposed surface.

35. The electromechanical microstructure according to claim 1, wherein the first organic film is in a material such that the exposed surface of the deformable zone covered with this film has biocompatibility, non cyctotoxicity, and/or anti-adhesion or cellular anti-proliferation functions.

36. The electromechanical microstructure according to claim 1, wherein the second organic film is a film with biocompatibility and non-cyctotoxicity functions.

37. A wafer comprising a series of the electromechanical microstructures according to claim 1, and comprising a first shared electrode electrically connecting all of the first mechanical parts of the series of the electromechanical microstructures.

38. A microsystem comprising the electromechanical microstructure according to claim 1, electrically assembled with a front face turned round on an interconnection support comprising an opening facing the deformable zone of the microstructure.

39. A The microsystem according to claim 38, wherein the support is formed from a wafer in silicon, and comprising a probe connected to a dedicated electronic component itself assembled on the support.

40. A microsystem comprising the electromechanical microstructure according to claim 1, electrically assembled with a front face turned round on an interconnection support comprising an opening facing the deformable zone of the microstructure a film of the annular zone of the microstructure being in an insulating thermofusible material and coming into contact with a substrate of the support to form a sealing joint around the deformable zone of the microstructure.

41. A The microsystem according to claim 40, wherein a substrate of the support comprises a film formed in a thermofusible insulating material obtained from an electro-initiated reaction, a part of the substrate coming into contact with the film of the annular zone of the microstructure to form a sealing joint around the deformable zone of the microstructure by heat sealing.

42. An electromechanical microstructure comprising:
a first mechanical part formed in a first electrically conductive material, and which comprises (1) a zone deformable in an elastic manner having a thickness value and an exposed surface and (2) a first organic film having a thickness, present on a whole of the exposed surface of the deformable zone,
wherein the first organic film is bonded in a covalent manner to the exposed surface of the deformable zone and formed from an electro-initiated reaction, and wherein the first electrically conductive material constituting the first mechanical part is a doped semi-conductor, and wherein a doping of type opposite to that of the first material defines an electrode contact at a surface of the first mechanical part outside of the exposed surface.

43. A wafer comprising a series of the electromechanical microstructures according to claim 42, and comprising a first shared electrode electrically connecting all of the electrode pads and wherein a polarity necessary to electro-initiate the organic films corresponds to an open sense of a diode created by the doping in a sense from the electrode contact towards the mechanical part.

44. A wafer comprising:
   a series of the electromechanical microstructures comprising,
      a first mechanical part formed in a first electrically conductive material, and which comprises (1) a zone deformable in an elastic manner having a thickness value and an exposed surface and (2) a first organic film having a thickness, present on a whole of the exposed surface of the deformable zone,
      wherein the first organic film is bonded in a covalent manner to the exposed surface of the deformable zone and formed from an electro-initiated reaction; and
   a first shared electrode electrically connecting all of the first mechanical parts of the series of the electromechanical microstructures.

* * * * *